(12) United States Patent
Baumann et al.

(10) Patent No.: US 10,519,099 B2
(45) Date of Patent: Dec. 31, 2019

(54) CYSTOBACTAMIDES

(71) Applicant: HELMHOLTZ-ZENTRUM FÜR INFEKTIONSFORSCHUNG GMBH, Braunschweig (DE)

(72) Inventors: Sascha Baumann, Hamburg (DE); Jennifer Herrmann, Saarbrücken (DE); Kathrin Mohr, Braunschweig (DE); Heinrich Steinmetz, Hildesheim (DE); Klaus Gerth, Braunschweig (DE); Ritesh Raju, Sydney (AU); Rolf Müller, Blieskastel (DE); Rolf Hartmann, Saarbrücken (DE); Mostafa Hamed, Saarbrücken (DE); Walid A. M. Elgaher, Saarbrücken (DE); Maria Moreno, Hannover (DE); Franziska Gille, Leimen (DE); Liang Liang Wang, Hannover (DE); Andreas Kirschning, Celle (DE); Stephan Hüttel, Braunschweig (DE)

(73) Assignee: HELMHOLTZ-ZENTRUM FÜR INFEKTIONSFORSCHUNG GMBH, Braunschweig (DE)

( * ) Notice: Subject to any disclaimer, the term of this patent is extended or adjusted under 35 U.S.C. 154(b) by 0 days.

(21) Appl. No.: 15/529,940

(22) PCT Filed: Nov. 26, 2015

(86) PCT No.: PCT/EP2015/002382
§ 371 (c)(1),
(2) Date: May 25, 2017

(87) PCT Pub. No.: WO2016/082934
PCT Pub. Date: Jun. 2, 2016

(65) Prior Publication Data
US 2017/0327458 A1 Nov. 16, 2017

(30) Foreign Application Priority Data
Nov. 26, 2014 (EP) .................................... 14003992

(51) Int. Cl.
| | | |
|---|---|---|
| *A61K 31/196* | (2006.01) | |
| *C07C 237/00* | (2006.01) | |
| *C07C 237/44* | (2006.01) | |
| *C12P 13/02* | (2006.01) | |
| *C12R 1/01* | (2006.01) | |
| *C12R 1/00* | (2006.01) | |

(52) U.S. Cl.
CPC .......... *C07C 237/44* (2013.01); *A61K 31/196* (2013.01); *C12P 13/02* (2013.01); *C12R 1/01* (2013.01); *C07C 237/00* (2013.01); *C12R 1/00* (2013.01)

(58) Field of Classification Search
CPC .................................................... A61K 31/196
See application file for complete search history.

(56) References Cited

U.S. PATENT DOCUMENTS

| | | | |
|---|---|---|---|
| 7,758,972 B2 | 7/2010 | Egawa et al. | |
| 2008/0145700 A1 | 6/2008 | Egawa et al. | |
| 2010/0178324 A1 | 7/2010 | Ahn | |
| 2017/0204052 A1 | 7/2017 | Kim et al. | |

FOREIGN PATENT DOCUMENTS

| | | |
|---|---|---|
| EP | 1867331 A1 | 12/2007 |
| JP | H11279163 A | 10/1999 |
| JP | 2004-501191 A | 1/2004 |
| JP | 2008-106044 A | 5/2008 |
| WO | 02/00216 A1 | 1/2002 |
| WO | 2004035760 A2 | 4/2004 |
| WO | 2013078277 A1 | 5/2013 |
| WO | 2014125075 A1 | 8/2014 |
| WO | 2015/003816 A2 | 1/2015 |
| WO | 2016-082934 A1 | 6/2016 |

OTHER PUBLICATIONS

Pommier, Y. et al., Chemistry & Biology 2010, 17, 421.
Azzarito et al., 2-O-Alkylated para-benzamide a-helix mimetics: the role of scaffold curvature†, Organic & Biomolecular Chemistry, 2012, 10, 6469-6472.
Fomovska et al., "Salicylanilide Inhibitors of Toxoplasma gondii", Journal of Medicinal Chemistry, 2012, 55, 8375-8391.
International Search Report dated Jan. 20, 2015 issued in International Application No. PCT/EP2014/001925, dated Jan. 20, 2015, 4 pages.
Adams (1983) J. Am. Chem. Soc. 105, No. 3.
Belousov (1997) Nucleic Acids Res. 25:3440-3444.
Frenkel (1995) Free Radic. Biol. Med. 19:373-380.
Blommers (1994) Biochemistry 33:7886-7896.
Narang (1979) Meth. Enzymol. 68:90.
Brown (1979) Meth. Enzymol. 68:109.
Beaucage (1981) Tetra. Lett. 22: 1859.
Kozak, 1991, J. Biol. Chem. 266:19867-19870.

(Continued)

*Primary Examiner* — Ana Z Muresan
(74) *Attorney, Agent, or Firm* — Mintz Levin Cohn Ferris Glovsky and Popeo, P.C.; Peter F. Corless

(57) ABSTRACT

The present invention provides a method for the treatment or prophylaxis of bacterial infections by administering to a subject in need thereof an effective amount of a compound of formula.

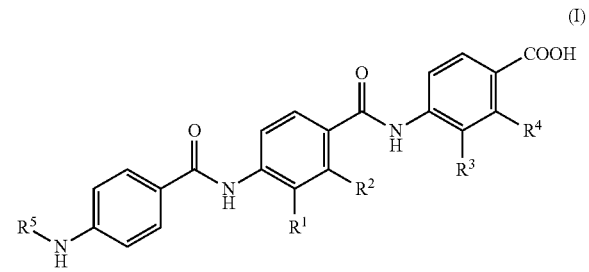

17 Claims, 2 Drawing Sheets

(56) References Cited

OTHER PUBLICATIONS

Figure 1:
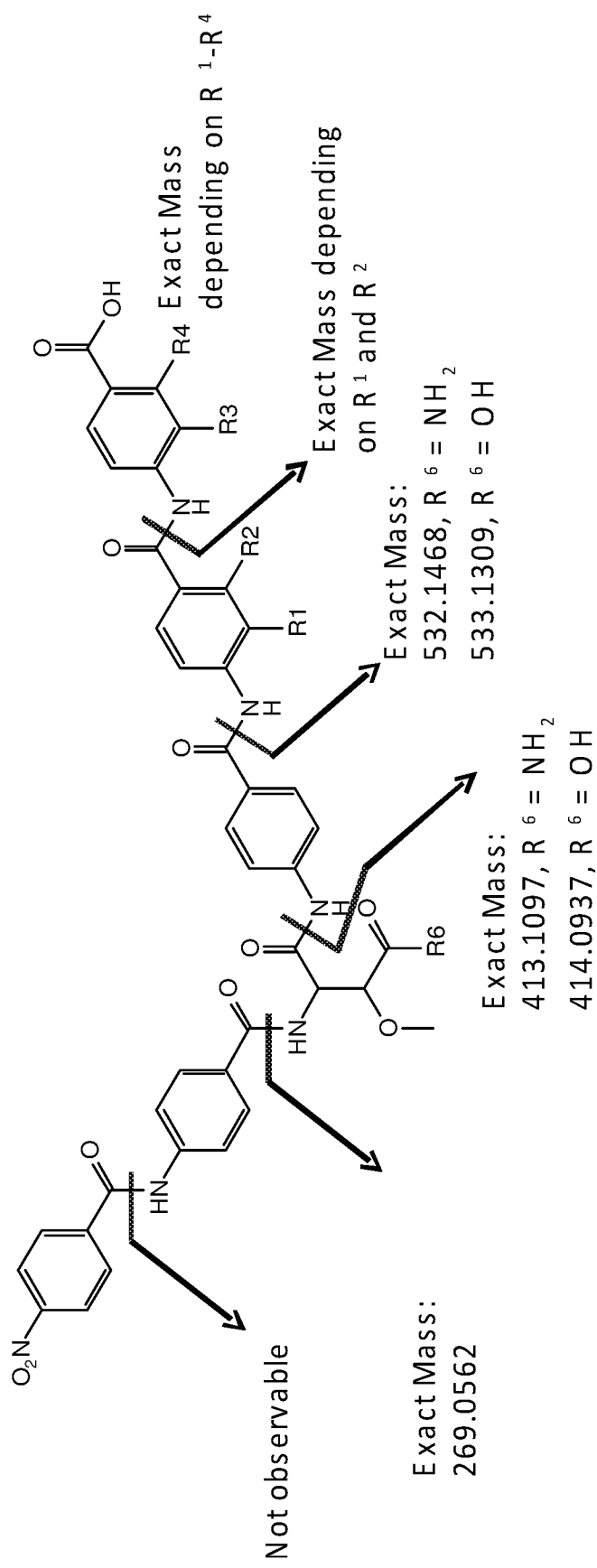

Gruger, T., et al., Antimicrob. Agents Chemother. 48, 2004, 4495-4504.
Schedletzky, H. et al., J. Antimicrob. Chemother. 43, 1999, 31-37.
Khodursky, A.B. et al., Proc. Natl. Acad. Sci. USA 92, 1995, 11801-11805.
Schulte, A. et al., J. Antimicrob. Chemother. 46, 2000, 1037-1046.
Keeney, D., et al., Antimicrob. Chemother. 61, 2008, 46-53.
Heisig, P. et al., Antimicrob. Agents Chemother. 37, 1993, 669-701.
Mosmann, T. et al., J. lmmunol. Meth. 65, 1983, 55-63.
Gould et al., Journal of Magnetic Resonance, Academic Press, London, GB, vol. 34, No. 1, Apr. 1, 1979, pp. 37-55.
International Search Report and Written Opinion—Internatonal Application No. PCT/EP2015/002382.
International Search Report issued in corresponding International Application No. PCT/EP2014/001925, dated Jan. 20, 2015, 8 pages.
Plante et al., "Oligobenzamide proteomimetic inhibitors of the p53-hDM2 proten-protein interaction," Chemical Communications. 34: 5091-5093 (2009).
"List of new names and new combinations previously effectively, but not validly, published," International Journal of Systematic and Evolutionary Microbiology. 57:893-897 (2007).
Mensa et al., "Antibacterial Mechanism of Action of Arylamide Foldamers," Antimicrobial Agents and Chemotherapy. 55(11): 5043-5053 (2011).
Kulikov et al., "Design and synthesis of oligamide-based double alfa-helix mimetics," European Journal of Organic Chemistry. 3433-3445 (2013).
Yap et al., "Relaxation of the rigid backbone of an oligamide-foldamer-based alfa-helix mimetic: identification of potent Bcl-xL inhibitors," Organic and Biomolecular Chemistry. 10: 2928-2933 (2012).
Seyler et al., "Tuning the solubility of hepta(p-benzamide)s via the monomer sequence," Tetrahedron Letters. 54(8): 753-756 (2013).
Beyer et al., "Metabolic diversity in myxobacteria: identification the myxalamid and the stigmatellin biosynthetic gene cluster of *Stigmatella aurantiaca* Sg a15 and a combined polyketide-(poly)peptide gene cluster from the epothilone producing strain Sorangium cellulosum So ce90," Biochim et Biophysica Acta. 1445(2): 189-195 (1999).
Database UniProt [Online] Jul. 5, 2004, "SubName: Full=Non-ribosomal peptide synthase;" XP002730995, retrieved from EBI accession No. UNIPROT:Q70C52, Database accession No. Q70C52 sequence.
Sambrook, ed., Molecular Cloning: A Laboratory Manual (2nd Ed.) vols. 1-3, Cold Spring Harbor Laboratory, (1989).
Current Protocols in Molecular Biology, Ausubel, ed. John Wiley & Sons, Inc., New York (1997).
Laboratory Techniques in Biochemistry and Molecular Biology: Hybridization With Nucleic Acid Probes, Part I. Theory and Nucleic Acid Preparation, Tijssen, ed. Elsevier, N.Y. (1993).
Goeddel, Gene Expression Technology: Methods in Enzymology 185, Academic Press, San Diego, CA (1990).
Davis, L. et al., Basic Methods in Molecular Biology (1986).
Vippagunta, S. R., Brittain, H. G., & Grant, D. J. (2001). Crystalline solids. Advanced drug delivery reviews, 48(1), 3-26.
Bohle, A. et al, Hydrogen-Bonded Aggregates of Oligoaramide? Poly(ethylene glycol) Block Copolymers. Macromolecules (2010) 43, 4978-4985.
Baumann, S. et al, "Cystobactamids: Myxobacterial Topoisomerase Inhibitors Exhibiting Potent Antibacterial Activity", Angew. Chem. Int. Ed. (2014) 53, 14605-14609.
International Search Report for International Patent Application No. PCT/EP2018/072817, dated Jan. 10, 2019, 7 pages.
Kretz, J. et al., "Total Synthesis of Albicidin: A Lead Structure from *Xanthomonas albilineans* for Potent Antibacterial Gyrase Inhibitors", Angew. Chem. Int. Ed. (2015) 54, 1969-1973.
Grätz, S. et al., "Synthesis and Antimicrobial Activity of Albicidin Derivatives with Variations of the Central Cyanoalanine Building Block", ChemMedChem (2016) 11, 1499-1502.
Kerwat, D. et al., "Synthesis of Albicidin Derivatives: Assessing the Role of N-terminal Acylation on the Antibacterial Activity", ChemMedChem (2016) 11, 1899-1903.
Kim, Y. J. et al., "Isolation of Coralmycins A and B, Potent Anti-Gram Negative Compounds from the Myxobacteria Corallococcus coralloides M23", Journal of Natural Products (2016) 79, 2223-2228.
Petras, D. et al., "The O-Carbamoyl-Transferase Alb15 is Responsible for the Modification of Albicidin", ACS Chem. Biol. (2016) 11, 1198-1204.
von Eckardstein, L. et al., "Total Synthesis and Biological Assessment of Novel Albicidins Discovered by Mass Spectrometric Networking" Chem. Eur. J. (2017) 23, 15316-15321.
Lakemeyer, M. et al., "Thinking Outside the Box—Novel Antibacterials to Tackle the Resistance Crisis", Angew. Chem. Int. Ed. (2018) 57, 2-39.
Bhattacharya, M. et al., "Second order nonlinearity in oligoamides", Synthetic Metals, 155 (2005) 389-392.
Japanese Office Action for Japanese Patent Application No. 2017-528464, dated Aug. 21, 2019, 7 pages, English translation.

CYSTOBACTAMIDES

This application is a National Phase application file under 35 U.S.C. § 371 of PCT International Application No. PCT/EP2015/002382 with an International Filing Date of Nov. 26, 2015, which claims under 35 U.S.C. § 119(a) the benefit of European Application No. 14003992.6, filed Nov. 26, 2014, the entire contents of which are incorporated herein by reference.

Cystobactamides are novel natural products that have been isolated from myxobacterium *Cystobacter velatus* (MCy8071; internal name: *Cystobacter ferrugineus*). Cystobactamides exhibit a good antibiotic activity, especially against selected Gram-negative bacteria, such as *E. coli, P. aeruginosa*, and *A. baumannii*, as well as a broad spectrum activity against Gram-positive bacteria.

The present invention provides compounds of formula (I)

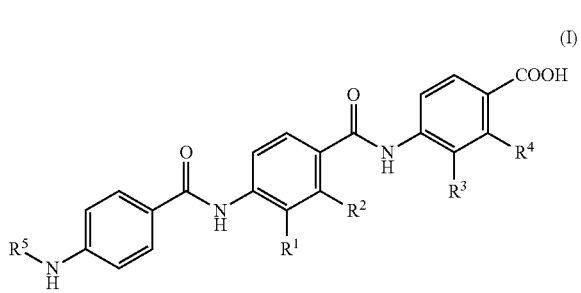

wherein
$R^1$ is hydrogen, OH or a group of formula —O—$C_{1-6}$ alkyl;
$R^2$ is hydrogen, OH or a group of formula —O—$C_{1-6}$ alkyl;
$R^3$ is hydrogen, OH or a group of formula —O—$C_{1-6}$ alkyl;
$R^4$ is hydrogen, OH or a group of formula —O—$C_{1-6}$ alkyl;
and
$R^5$ is a hydrogen atom or a group of the following formula:

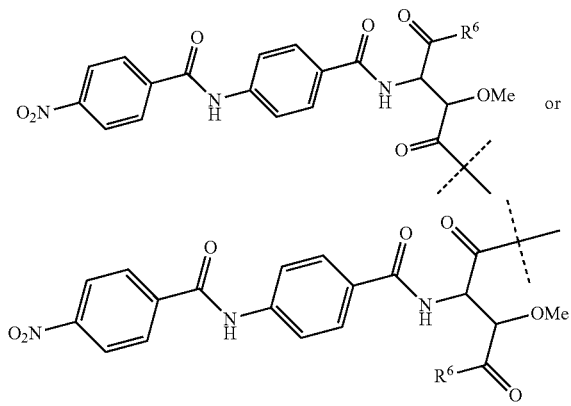

wherein $R^6$ is OH or $NH_2$;
or a pharmaceutically acceptable salt, solvate or hydrate or a pharmaceutically acceptable formulation thereof.

The expression $C_{1-6}$ alkyl refers to a saturated, straight-chain or branched hydrocarbon group that contains from 1 to 6 carbon atoms. The expression $C_{1-4}$ alkyl refers to a saturated, straight-chain or branched hydrocarbon group that contains from 1 to 4 carbon atoms. Examples are a methyl (Me), ethyl, propyl, iso-propyl, n-butyl, iso-butyl, sec-butyl or tert-butyl group.

Preferred are compounds of formula (I) wherein
$R^1$ is hydrogen, OH or a group of formula —O—$C_{1-4}$ alkyl;
$R^2$ is hydrogen, OH or a group of formula —O—$C_{1-4}$ alkyl;
$R^3$ is hydrogen, OH or a group of formula —O—$C_{1-4}$ alkyl;
$R^4$ is hydrogen, OH or a group of formula —O—$C_{1-4}$ alkyl;
and
$R^5$ is a group of the following formula:

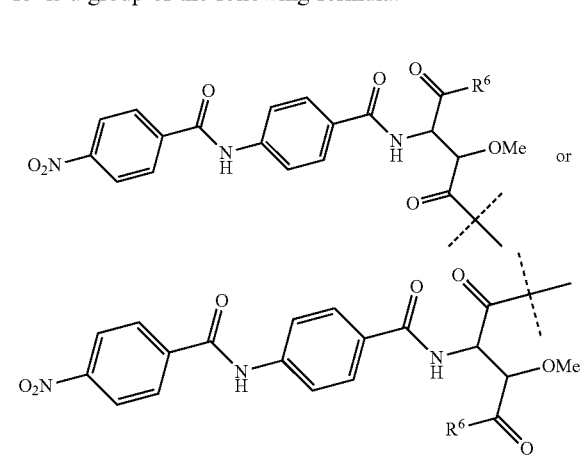

wherein $R^6$ is OH or $NH_2$;
or a pharmaceutically acceptable salt, solvate or hydrate or a pharmaceutically acceptable formulation thereof.

Preferred are compounds of formula (I) wherein $R^1$ is OH.

Moreover preferred are Compounds of formula (I) wherein $R^1$ is a group of formula —O—$C_{1-4}$ alkyl; especially wherein $R^1$ is a group of formula —O—$CH(CH_3)_2$.

Further preferred are compounds of formula (I) wherein $R^2$ is hydrogen.

Moreover preferred are compounds of formula (I) wherein $R^2$ is OH.

Further preferred are compounds of formula (I) wherein $R^3$ is hydrogen.

Moreover preferred are compounds of formula (I) wherein $R^3$ is OH.

Further preferred are compounds of formula (I) wherein $R^3$ is a group of formula —O—$C_{1-4}$ alkyl.

Moreover preferred are compounds of formula (I) wherein $R^4$ is hydrogen.

Further preferred are compounds of formula (I) wherein $R^4$ is OH.

Especially preferred are compounds of formula (I) wherein $R^5$ is a group of the following formula:

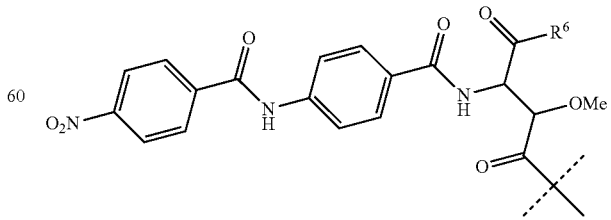

wherein $R^6$ is OH or $NH_2$.

Moreover especially preferred are compounds of formula (I) wherein $R^5$ is a group of the following formula:

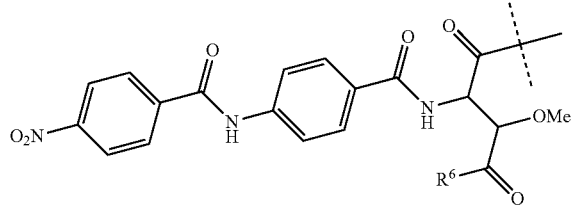

wherein $R^6$ is OH or $NH_2$.

Especially preferred are compounds of formula (II):

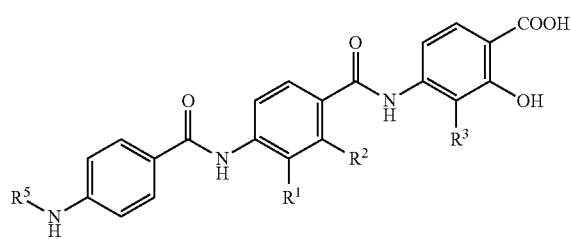

wherein $R^1$, $R^2$, $R^3$ and $R^5$ are as defined above for compounds of formula (I), or a pharmaceutically acceptable salt, solvate or hydrate or a pharmaceutically acceptable formulation thereof.

Moreover especially preferred are compounds of formula (III):

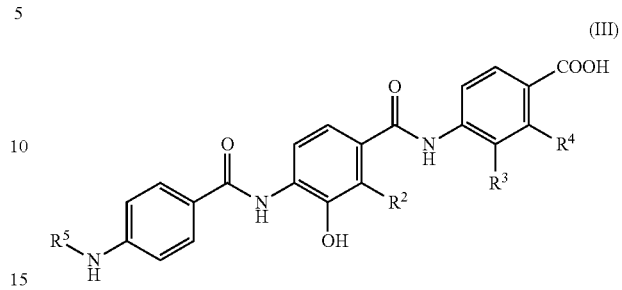

wherein $R^2$, $R^3$, $R^4$ and $R^5$ are as defined above for compounds of formula (I), or a pharmaceutically acceptable salt, solvate or hydrate or a pharmaceutically acceptable formulation thereof.

Moreover especially preferred are compounds of formula (IV):

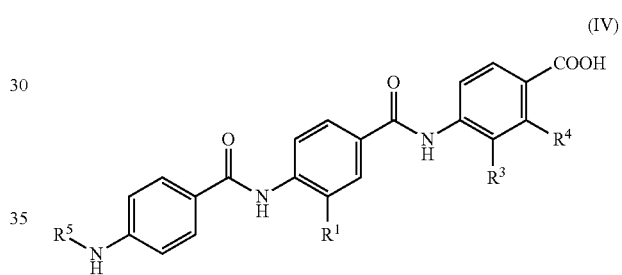

wherein $R^1$, $R^3$, $R^4$ and $R^5$ are as defined above for compounds of formula (I), or a pharmaceutically acceptable salt, solvate or hydrate or a pharmaceutically acceptable formulation thereof.

Most preferred are the following compounds:

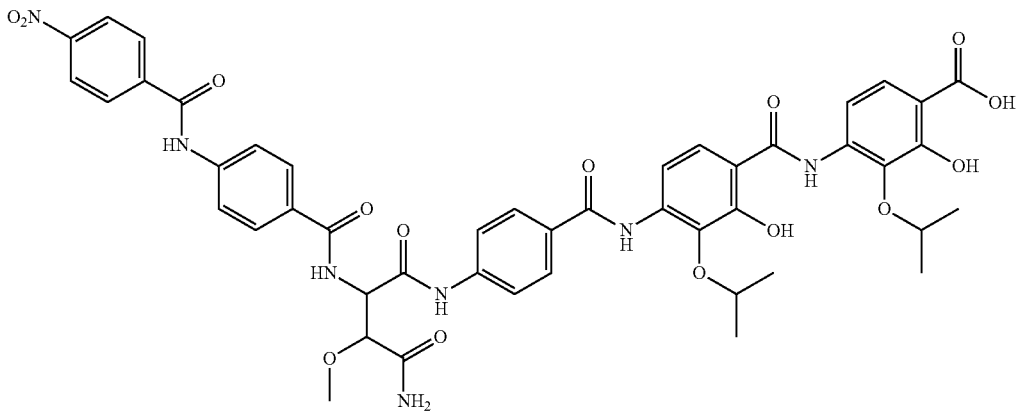

Chemical Formula: $C_{46}H_{45}N_7O_{15}$
Exact Mass: 935.2974

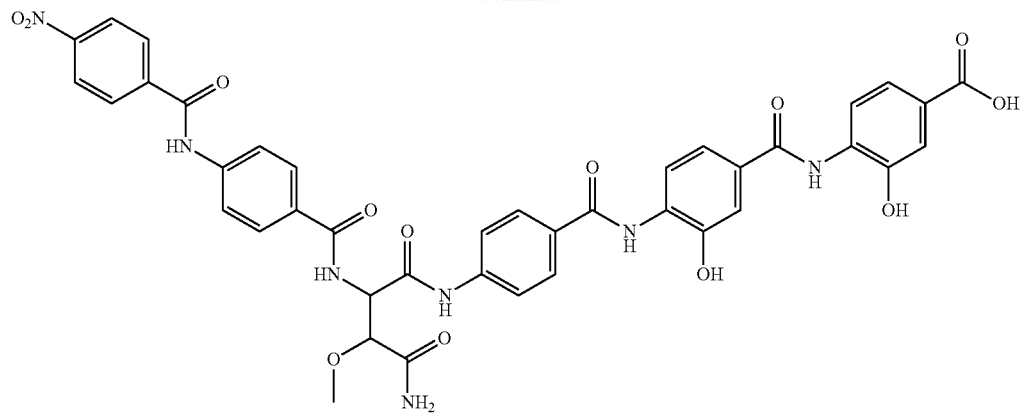
Chemical Formula: C₄₀H₃₃N₇O₁₃
Exact Mass: 819.2136
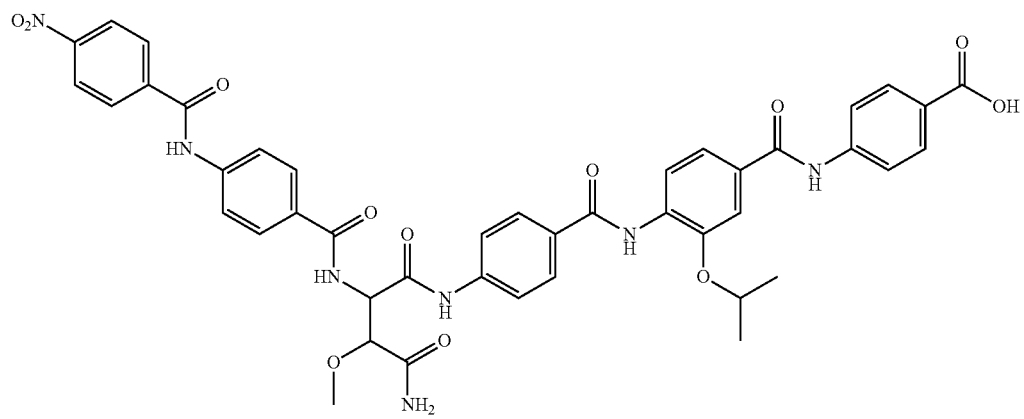
Chemical Formula: C₄₃H₃₉N₇O₁₂
Exact Mass: 845.2657
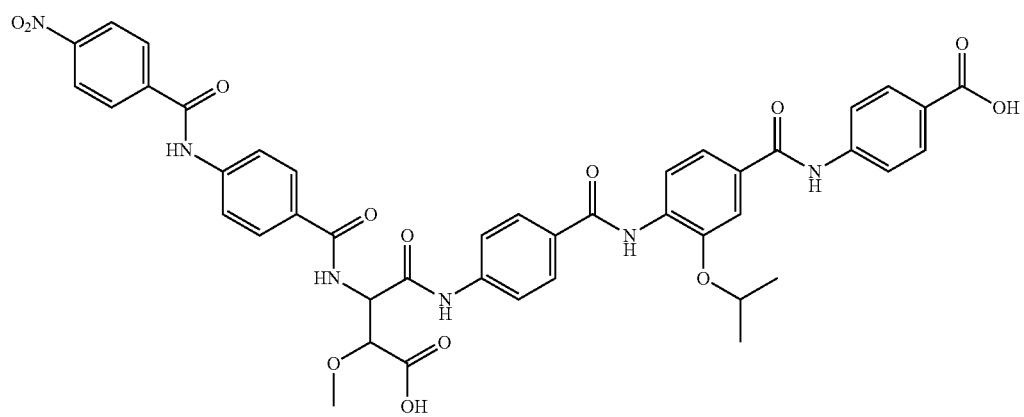
Chemical Formula: C₄₃H₃₈N₆O₁₃
Exact Mass: 846.2497

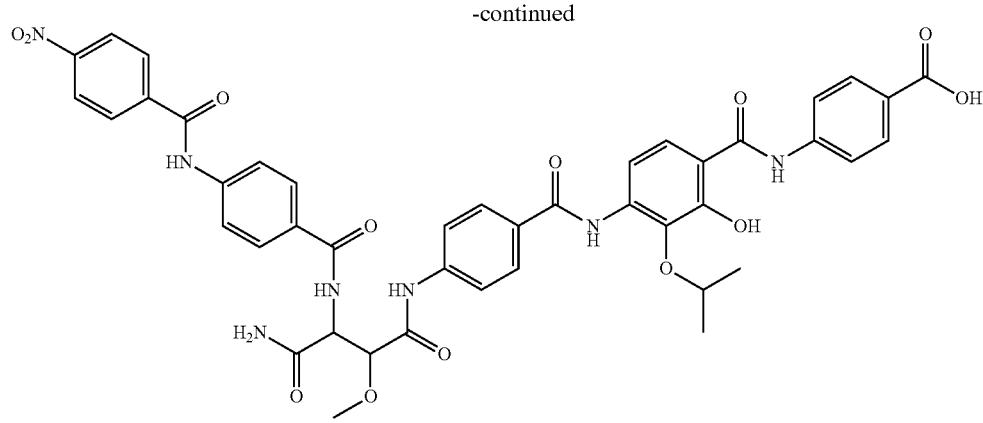
Chemical Formula: C₄₃H₃₉N₇O₁₃
Exact Mass: 861.2606
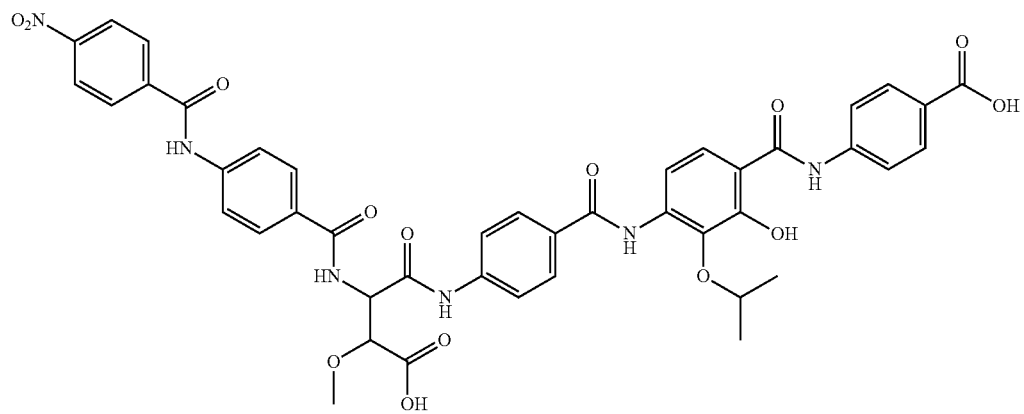
Chemical Formula: C₄₃H₃₈N₆O₁₄
Exact Mass: 862.2446
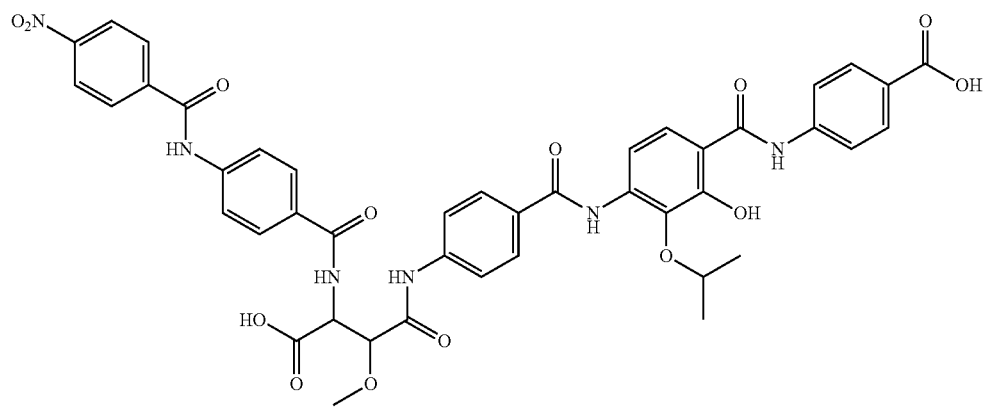
Chemical Formula: C₄₃H₃₈N₆O₁₄
Exact Mass: 862.2446

-continued
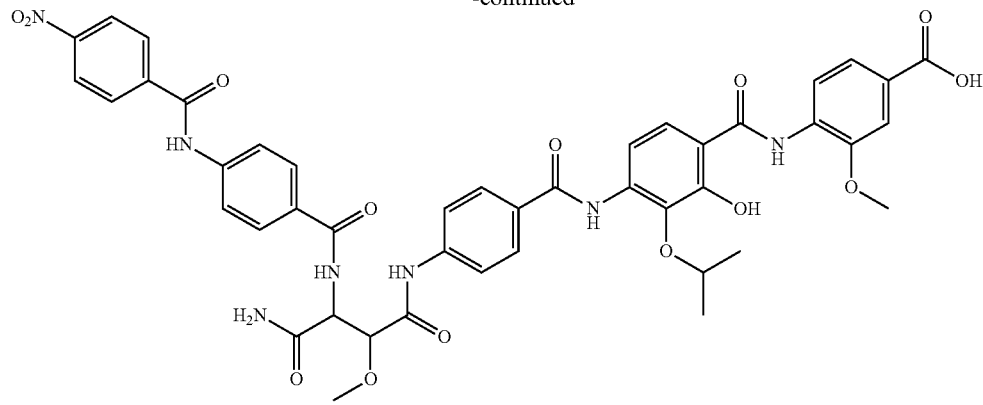
Chemical Formula: $C_{44}H_{41}N_7O_{14}$
Exact Mass: 891.2711
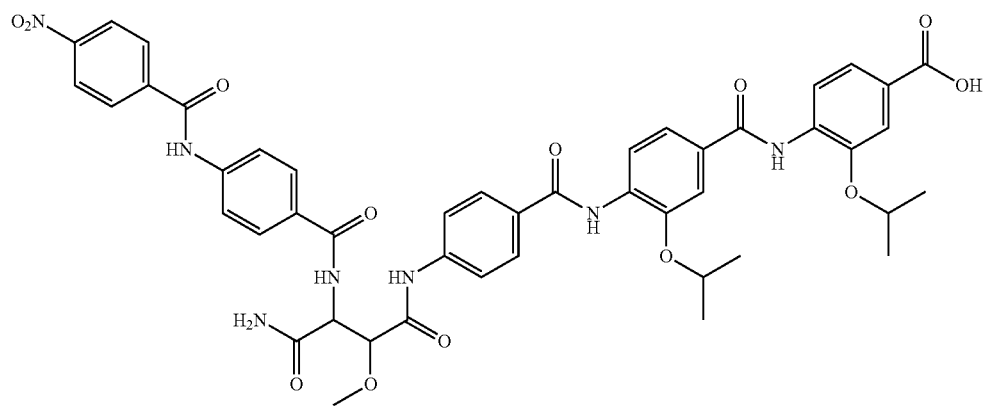
Chemical Formula: $C_{46}H_{45}N_7O_{13}$
Exact Mass: 903.3075
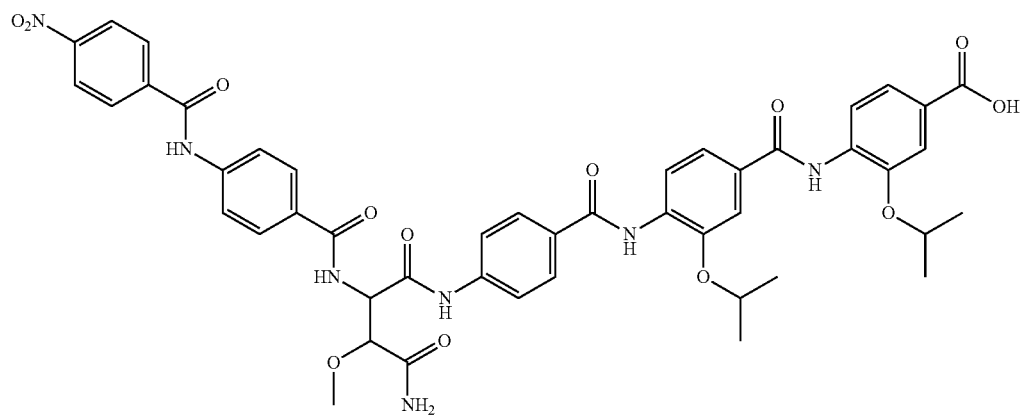
Chemical Formula: $C_{46}H_{45}N_7O_{13}$
Exact Mass: 903.3075

-continued
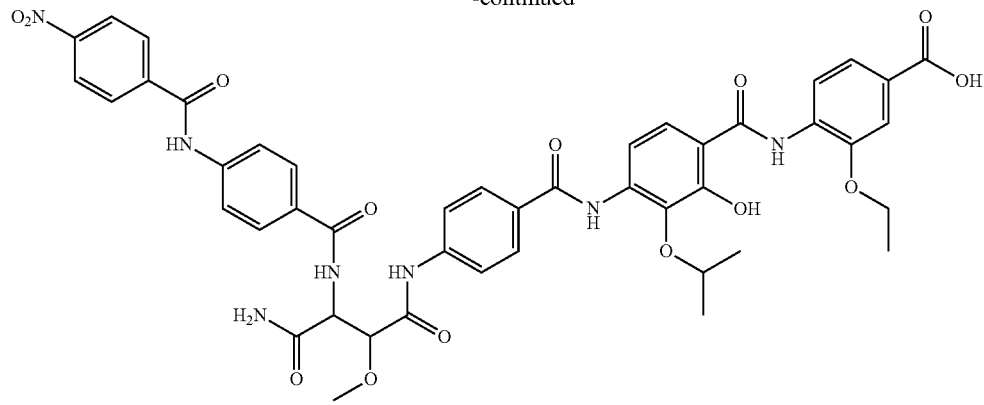
Chemical Formula: C₄₅H₄₃N₇O₁₄
Exact Mass: 905.2868
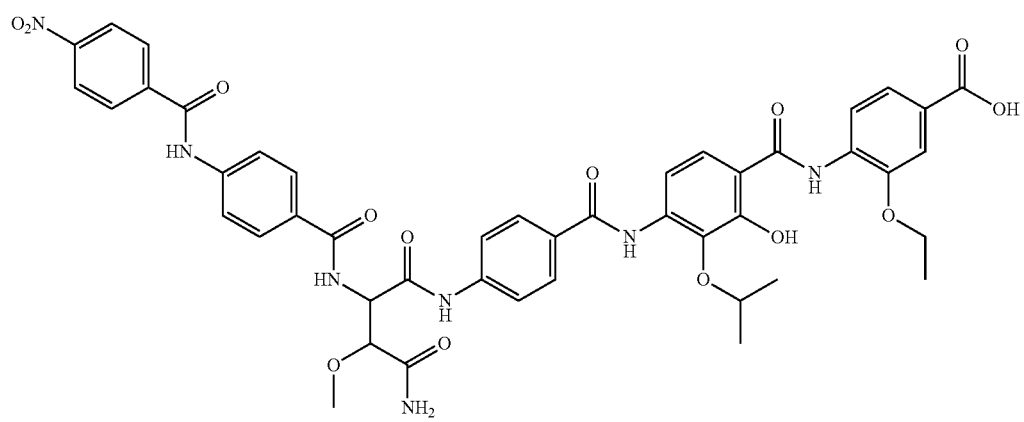
Chemical Formula: C₄₅H₄₃N₇O₁₄
Exact Mass: 905.2868
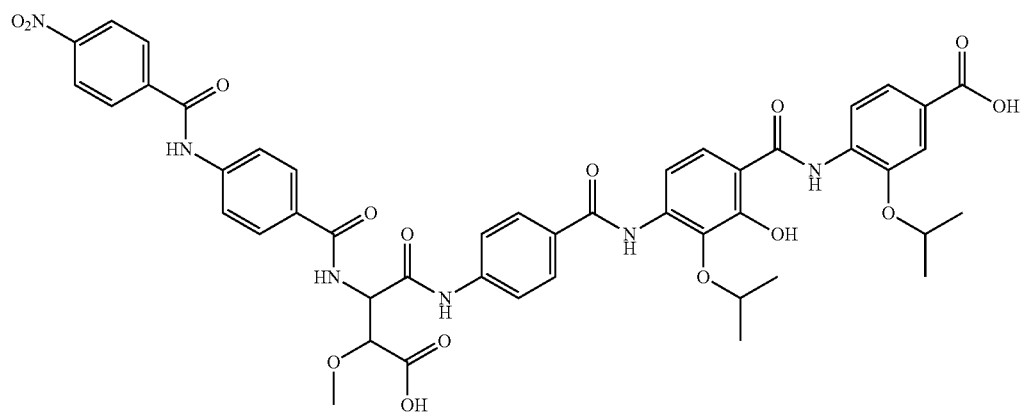
Chemical Formula: C₄₆H₄₄N₆O₁₅
Exact Mass: 920.2865

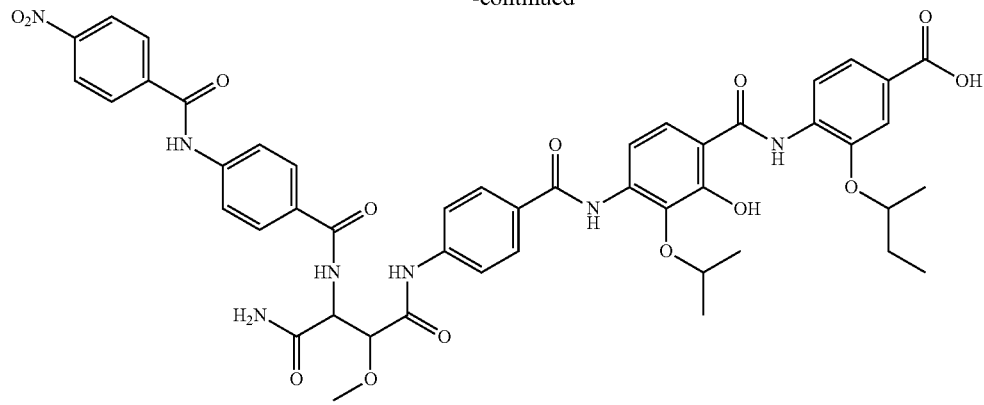
Chemical Formula: C₄₇H₄₇N₇O₁₄
Exact Mass: 933.3181
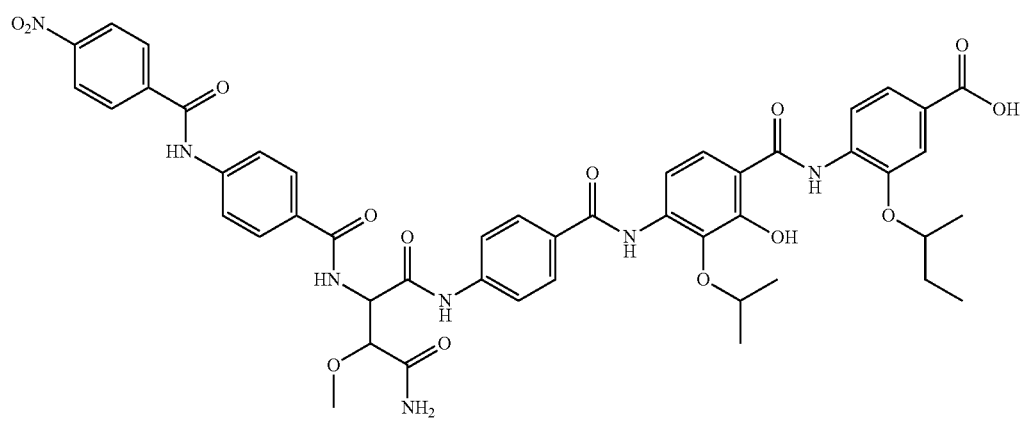
Chemical Formula: C₄₇H₄₇N₇O₁₄
Exact Mass: 933.3181
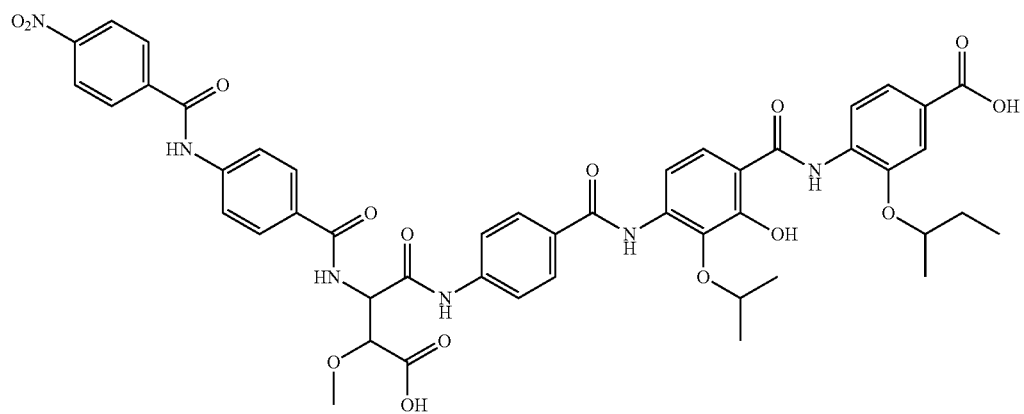
Chemical Formula: C₄₇H₄₆N₆O₁₅
Exact Mass: 934.3021

-continued
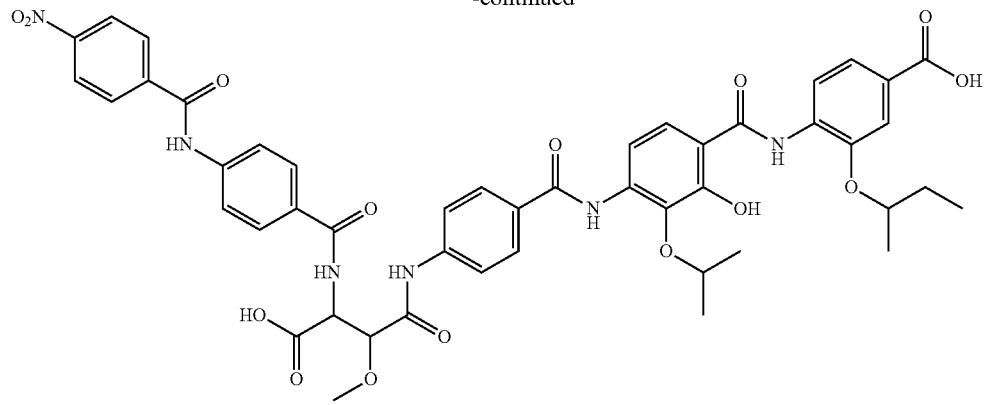
Chemical Formula: C$_{47}$H$_{46}$N$_6$O$_{15}$
Exact Mass: 934.3021
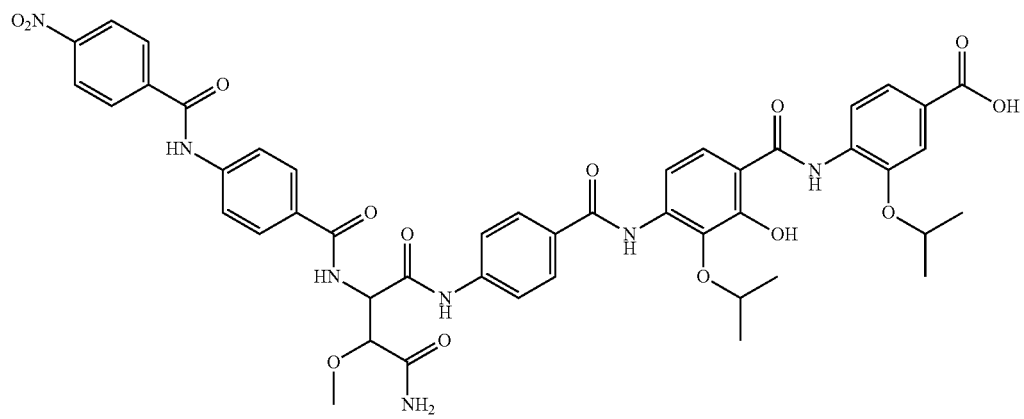
Chemical Formula: C$_{46}$H$_{45}$N$_7$O$_{14}$
Exact Mass: 919.3024
According to an especially preferred embodiment, the compounds of the present invention described herein show the following stereochemistry at group R$^5$:
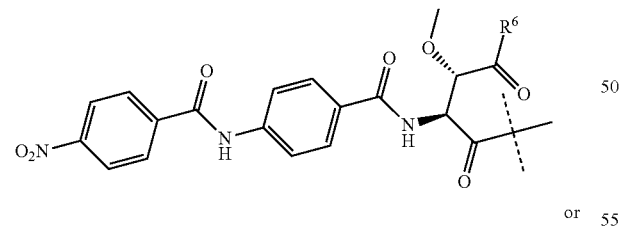
or
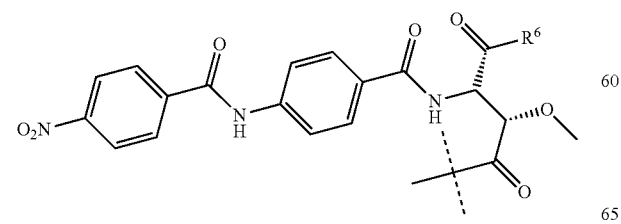
wherein R$^6$ is OH or NH$_2$.

Preferably, the following compounds are excluded from the scope of the present application:
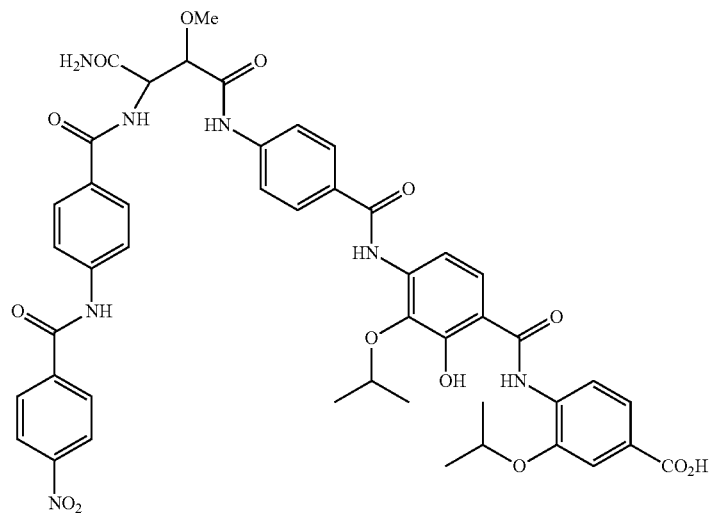
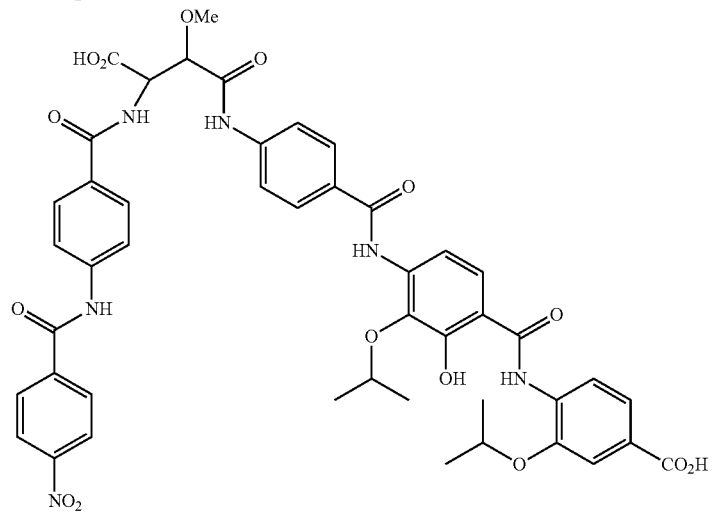
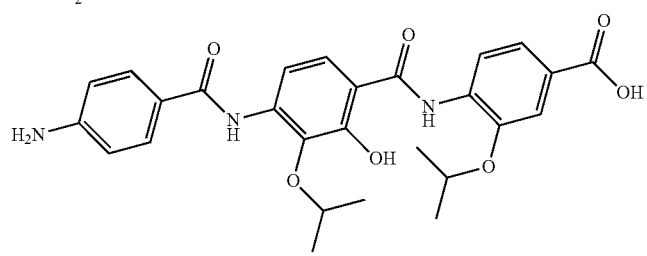
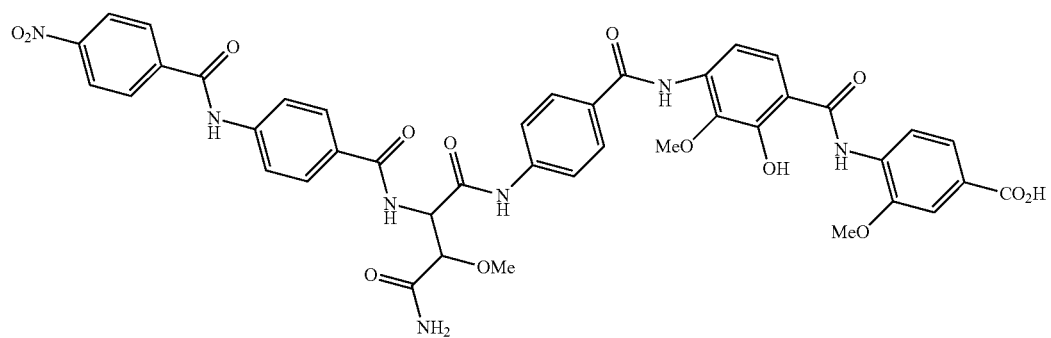

-continued
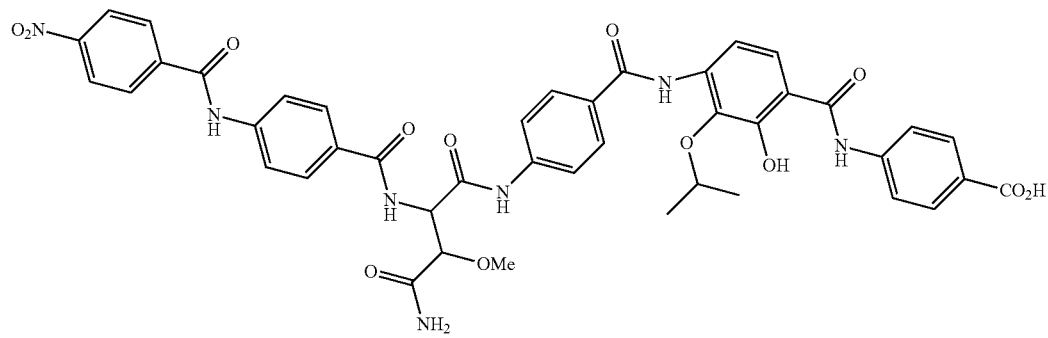
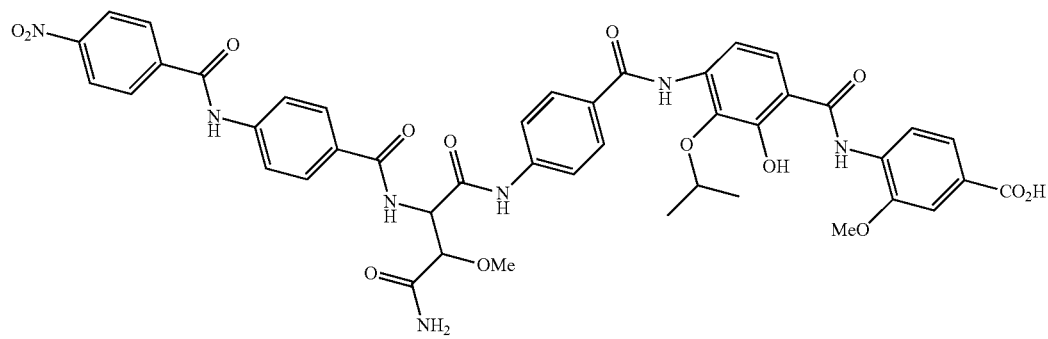
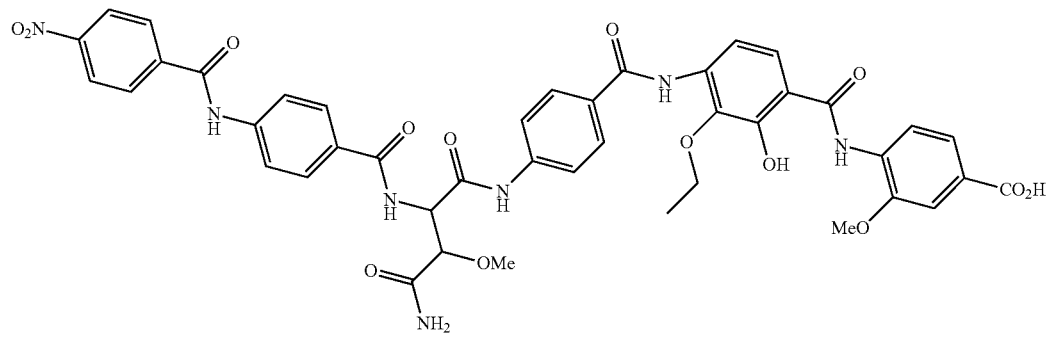
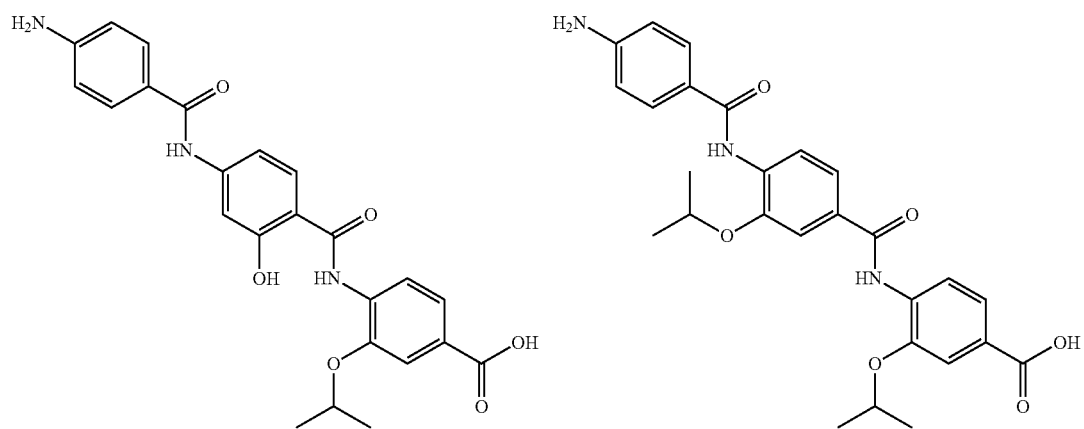

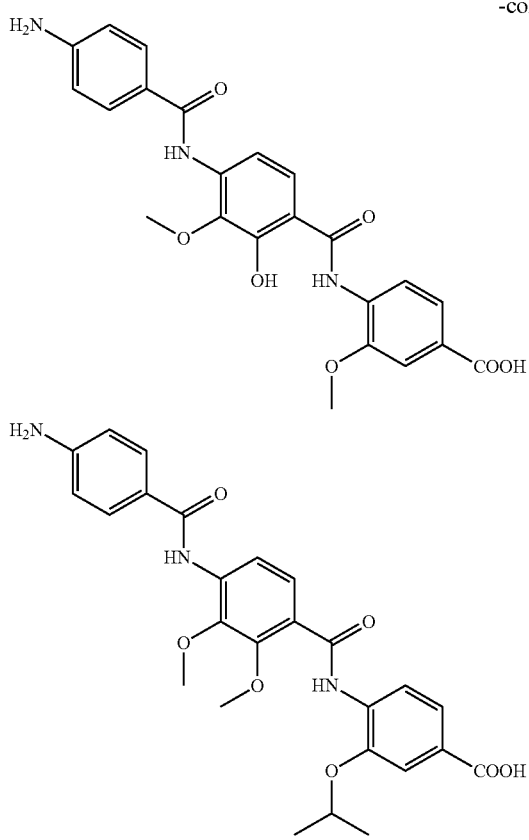

-continued

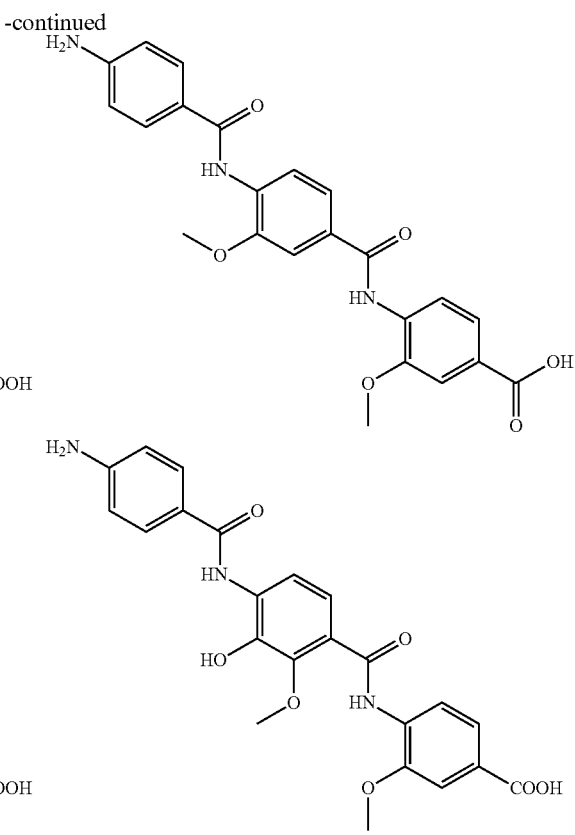

According to a further preferred embodiment, $R^1$, $R^2$, $R^3$, $R^4$ and $R^5$ are not at the same time hydrogen.

Moreover preferably, the following compound is excluded from the scope of the present application:

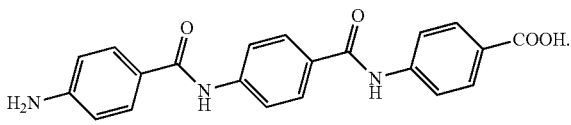 [SMILES: Nc1ccc(C(=O)Nc2ccc(C(=O)Nc3ccc(C(=O)O)cc3)cc2)cc1]

The present invention further provides pharmaceutical compositions comprising one or more compounds described herein or a pharmaceutically acceptable salt, solvate or hydrate thereof, optionally in combination with one or more carrier substances and/or one or more adjuvants.

The present invention furthermore provides compounds or pharmaceutical compositions as described herein for use in the treatment and/or prophylaxis of bacterial infections, especially caused by *E. coli, P. aeruginosa, A. baumannii*, other Gram-negative bacteria, and Gram-positive bacteria.

Moreover preferably, the present invention provides compounds for use in the treatment and/or prophylaxis of bacterial infections, especially caused by *Pseudomonas aeruginosa* and other Gram-negative bacteria.

It is a further object of the present invention to provide a compound as described herein or a pharmaceutical composition as defined herein for the preparation of a medicament for the treatment and/or prophylaxis of bacterial infections, especially caused by selected Gram-negative bacteria and Gram-positive bacteria.

Examples of pharmacologically acceptable salts of sufficiently basic compounds are salts of physiologically acceptable mineral acids like hydrochloric, hydrobromic, sulfuric and phosphoric acid; or salts of organic acids like methanesulfonic, p-toluenesulfonic, lactic, acetic, trifluoroacetic, citric, succinic, fumaric, maleic and salicylic acid. Further, a sufficiently acidic compound may form alkali or earth alkali metal salts, for example sodium, potassium, lithium, calcium or magnesium salts; ammonium salts; or organic base salts, for example methylamine, dimethylamine, trimethylamine, triethylamine, ethylenediamine, ethanolamine, choline hydroxide, meglumin, piperidine, morpholine, tris-(2-hydroxyethyl)amine, lysine or arginine salts; all of which are also further examples of salts of the compounds described herein. The compounds described herein may be solvated, especially hydrated. The hydratization/hydration may occur during the process of production or as a consequence of the hygroscopic nature of the initially water free compounds. The solvates and/or hydrates may e.g. be present in solid or liquid form.

The therapeutic use of the compounds described herein, their pharmacologically acceptable salts, solvates and hydrates, respectively, as well as formulations and pharmaceutical compositions also lie within the scope of the present invention.

The pharmaceutical compositions according to the present invention comprise at least one compound described herein and, optionally, one or more carrier substances and/or adjuvants.

As mentioned above, therapeutically useful agents that contain compounds described herein, their solvates, salts or formulations are also comprised in the scope of the present invention. In general, the compounds described herein will be administered by using the known and acceptable modes known in the art, either alone or in combination with any other therapeutic agent.

For oral administration such therapeutically useful agents can be administered by one of the following routes: oral, e.g. as tablets, dragees, coated tablets, pills, semisolids, soft or hard capsules, for example soft and hard gelatine capsules, aqueous or oily solutions, emulsions, suspensions or syrups, parenteral including intravenous, intramuscular and subcutaneous injection, e.g. as an injectable solution or suspension, rectal as suppositories, by inhalation or insufflation, e.g. as a powder formulation, as microcrystals or as a spray (e.g. liquid aerosol), transdermal, for example via an transdermal delivery system (TDS) such as a plaster containing the active ingredient or intranasal. For the production of such tablets, pills, semisolids, coated tablets, dragees and hard, e.g. gelatine, capsules the therapeutically useful product may be mixed with pharmaceutically inert, inorganic or organic excipients as are e.g. lactose, sucrose, glucose, gelatine, malt, silica gel, starch or derivatives thereof, talc, stearinic acid or their salts, dried skim milk, and the like. For the production of soft capsules one may use excipients as are e.g. vegetable, petroleum, animal or synthetic oils, wax, fat, and polyols. For the production of liquid solutions, emulsions or suspensions or syrups one may use as excipients e.g. water, alcohols, aqueous saline, aqueous dextrose, polyols, glycerin, lipids, phospholipids, cyclodextrins, vegetable, petroleum, animal or synthetic oils. Especially preferred are lipids and more preferred are phospholipids (preferred of natural origin; especially preferred with a particle size between 300 to 350 nm) preferred in phosphate buffered saline (pH=7 to 8, preferred 7.4). For suppositories one may use excipients as are e.g. vegetable, petroleum, animal or synthetic oils, wax, fat and polyols. For aerosol formulations one may use compressed gases suitable for this purpose, as are e.g. oxygen, nitrogen and carbon dioxide. The pharmaceutically useful agents may also contain additives for conservation, stabilization, e.g. UV stabilizers, emulsifiers, sweetener, aromatizers, salts to change the osmotic pressure, buffers, coating additives and antioxidants.

In general, in the case of oral or parenteral administration to adult humans weighing approximately 80 kg, a daily dosage of about 1 mg to about 10,000 mg, preferably from about 5 mg to about 1,000 mg, should be appropriate, although the upper limit may be exceeded when indicated. The daily dosage can be administered as a single dose or in divided doses, or for parenteral administration, it may be given as continuous infusion or subcutaneous injection.

The compounds of the present invention can be prepared by fermentation (e.g. by fermentation of strain MCy8071 DSM27004) or by chemical synthesis applying procedures known to a person skilled in the art.

The compounds of the present invention may be synthesised according to procedures described in PCT/EP2014/001925 (WO 2015/003816), especially on pages 87 to 138, which are incorporated herein by reference.

For example the compounds of the present invention can be prepared according to the following procedures:

EXAMPLES

1. Fermentation

Conditions of Production
Strain for Production

The strain *Cystobacter velatus* MCy8071 belongs to the order Myxococcales (Myxobacteria), suborder Cystobacterineae, family Cystobacteraceae, genus *Cystobacter*. The comparison of the partial 16S rRNA gene sequences with sequences of a public database (BLAST, Basic Local Alignment Search Tool provided by NCBI, National Center for Biotechnology Information) revealed 100% similarity to *Cystobacter velatus* strain DSM 14718.

MCy8071 was isolated at the Helmholtz Centre for Infection Research (HZI, formerly GBF) from a Chinese soil sample collected in 1982. The strain was deposited at the German Collection of Microorganisms in Braunschweig (DSM) in March 2013 under the designation DSM 27004.

Cultivation

The strain MCy8071 grows well on yeast-agar (VY/2: 0.5% *Saccharomyces cerevisiae*, 0.14% $CaCl_2 \times 2$ $H_2O$, 0.5 µg vitamine $B_{12}$/l, 1.5% agar, pH 7.4), CY-agar (casitone 0.3%, yeast extract 0.1%, $CaCl_2 \times 2$ $H_2O$ 0.1%, agar 1.5%, pH 7.2) and P-agar (peptone Marcor 0.2%, starch 0.8%, single cell protein probione 0.4%, yeast extract 0.2%, $CaCl_2 \times 2$ $H_2O$ 0.1%, $MgSO_4$ 0.1%, Fe-EDTA 8 mg/l, 1.5% agar, pH 7.5). The working culture was nurtured in liquid medium CY/H (50% CY-medium+50 mM Hepes, 50% H-medium: soy flour 0.2%, glucose 0.8%, starch 0.2%, yeast extract 0.2%, $CaCl_2 \times 2$ $H_2O$ 0.1%, $MgSO_4$ 0.1%, Fe-EDTA 8 mg/l, Hepes 50 mM pH 7.4). Liquid cultures were shaken at 180 rpm at 30° C. For conservation aliquots a 2 ml of a three days old culture were stored at −80° C. Reactivation, even after several years, is no problem on the above mentioned agar plates or in 20 ml CY/H-medium (in 100 ml Erlenmeyer flasks with plugs and aluminium-cap). After one-two days the 20 ml cultures can be upscaled to 100 ml.

Morphological Description

After two days in liquid medium CY/H the rod-shaped cells of strain MCy8071 have a length of 9.0-14.5 µm and width of 0.8-1.0 µm. On the above mentioned agar-plates swarming is circular. On VY/2-agar the swarm is thin and transparent. Yeast degradation is visible on VY/2-agar. On CY-agar the culture looks transparent-orange. On P-agar cell mass production is distinctive and swarming behaviour is reduced. The colony colour is orange-brown. Starch in P-agar is degraded.

MCy8071 is resistant against the following antibiotics: ampicillin, gentamycin, hygromycin, polymycin, bacitracin, spectinomycin, neomycin, and fusidinic acid. Weak growth is possible with cephalosporin and kasugamycin and no growth is possible with thiostrepton, trimethoprin, kanamycin, and oxytetracycline (final concentration of all antibiotics was adjusted to 50 µg $ml^{-1}$).

Production of Cystobactamides

The strain produces in complex media. He prefers nitrogen containing nutrients like single cell protein (Probion) and products of protein decomposition like peptone, tryptone, yeast extract, soy flour and meat extract. Here the production is better with several of the mentioned protein mixtures compared to a single one.

Cystobactamides are produced within the logarithmical to the stationary phase of growth. After two days in 100 liter fermentation (medium E) the amount of products did not increase anymore.

Cystobactamides are delivered to the medium and bind to XAD-adsorber resin. XAD is sieved by a metal sieve and eluted in acetone. Different production temperatures were tested (21° C., 30° C., 37° C. and 42° C.) whereby at 42° C. no production was possible. The optimal temperature was at 30° C. with maximal aeration.

Fermentation of MCy8071 was conducted in a 150 liter fermenter with 100 liter medium E (skimmed milk 0.4%, soy flour 0.4%, yeast extract 0.2%, starch 1.0%, $MgSO_4$ 0.1%, Fe-EDTA 8 mg/l, glycerine 0.5%; pH 7.4) and in a 100 liter fermenter with 70 liter medium M (soy-peptone 1.0%, maltose 1.0%, $CaCl_2 \times 2\ H_2O$ 0.1%, $MgSO_4$ 0.1%, Fe-EDTA 8 mg/l; pH 7.2) for four days at 30° C. The pH was regulated with potassium hydroxide (2.5%) and sulfuric acid between 7.2 and 7.4. The stirrer speed was 100-400 rpm, aerated with 0.05 vvm compressed air. The dissolved oxygen content within the fermentation broth was regulated by the stirrer speed to $pO_2$ 40%. To bind cystobactamides 1% adsorber resin was added to the fermentation broth. The fermenter was inoculated with 5 liter of a three days old pre-culture (E or M-medium, respectively). The production during the fermentation process was checked by HPLC-MS-analyses and serial dilution test of the methanol extract against *Escherichia coli*. The strain produces Cystobactamides.

The following Cystobactamides (in addition to Cystobactamides A, B, C, D, E and F described in WO 2015/003816=PCT/EP2014/001925) have been isolated and characterized by NMR and MS:

Cystobactamide 935-2:

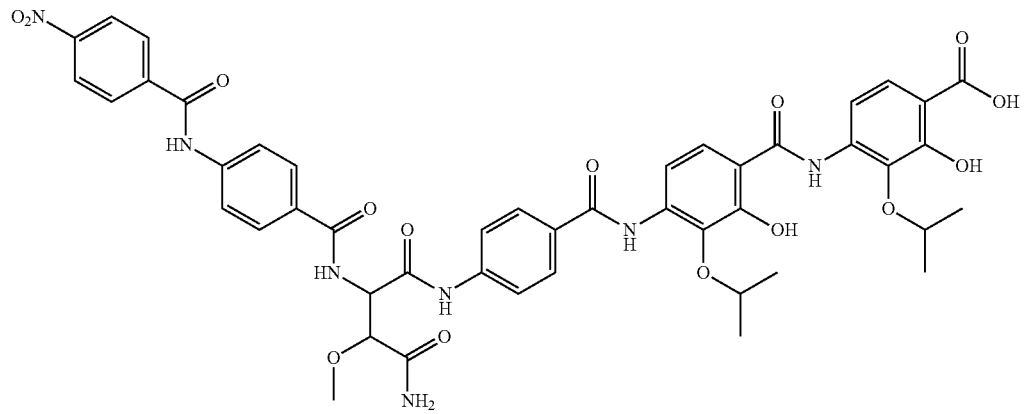

Chemical Formula: $C_{46}H_{45}N_7O_{15}$
Exact Mass: 935.2974

MS:

| Fragment/ion | Observed |
|---|---|
| 269.0562 | 269.0591 |
| 413.1097 | 413.1129 |
| 532.1468 | 532.1506 |
| 725.2207 | 725.2256 |
| 936.3046 | 936.3152 |

NMR:
Cystobactamide 935_2 NMR (700 MHz, MeOH-$d_4$)

| Substituent Nr. from Carboxyterminus | pos. | $\delta_H$, mult (J in Hz) | $\delta_C$* | COSY | HMBC |
|---|---|---|---|---|---|
| 1 | | 4-amino-2-hydroxy-3-isopropoxy-benzoic acid | | | |
| | 1 | — | 173.5 | — | — |
| | 2 | — | 110.9 | — | — |

-continued

| Substituent Nr. from Carboxyterminus | pos. | $\delta_H$, mult (J in Hz) | $\delta_C$* | COSY | HMBC |
|---|---|---|---|---|---|
| | 3 | — | 152.9 | — | — |
| | 4 | — | 155.7 | — | — |
| | 5 | — | 139.2 | — | — |
| | 6 | 8.00 d (8.89) | 111.8 | 7 | 2, 4 |
| | 7 | 7.65 d (8.89) | 126.1 | 6 | 1, 3, 5 |
| isopropoxy | 8 | 4.81 m | 75.9 | 9a/9b | 4, 9a/9b |
| isopropoxy | 9a/9b | 1.35 d (6.20) | 22.4 | 8 | 8, 9a/9b |
| 2' | | 4-amino-2-hydroxy-3-isopropoxy-benzoic acid | | | |
| | 1' | — | 166.3 | — | — |
| | 2' | — | 116.8 | — | — |
| | 3' | — | 152.4 | — | — |
| | 4' | — | 138.8 | — | — |
| | 5' | — | 137.4 | — | — |
| | 6' | 7.72 d (8.85) | 115.0 | 7' | 2', 4' |
| | 7' | 7.82 d (8.86) | 125.5 | 6' | 1', 3', 5' |
| isopropoxy | 8' | 4.51 m | 77.1 | 9a/9b' | 4', 9a/9b' |
| isopropoxy | 9a/9b' | 1.35 d (6.20) | 22.4 | 8' | 8', 9a/9b' |
| 3" | | 4-amino-benzoic acid | | | |
| | 1" | — | 166.9 | — | — |
| | 2" | — | 130.5 | — | — |
| | 3a/3b" | 7.97 d (8.70) | 129.1 | 4a/4b" | 1", 3a/3b", 5" |
| | 4a/4b" | 7.48 d (8.70) | 120.7 | 3a/3b" | 2", 4a/4b" |
| | 5" | — | 143.1 | — | — |
| 4''' | | asparagine | | | |
| | 1''' | — | 169.6 | — | — |
| | 2''' | 5.07 d (7.44) | 57.2 | 3''' | 1''', 3''', 4''', 1'''' |
| | 3''' | 4.18 d (7.46) | 82.0 | 2''' | 1''', 2''', 4''', 5''' |
| | 4''' | — | 174.4 | — | — |
| methoxy | 5''' | 3.50 s | 59.2 | — | 3''' |
| 5'''' | | 4-amino-benzoic acid | | | |
| | 1'''' | — | 169.0 | — | — |
| | 2'''' | — | 130.4 | — | — |
| | 3a/3b'''' | 7.93 d (8.84) | 129.3 | 4a/4b'''' | 1'''', 3a/3b'''', 5'''' |
| | 4a/4b'''' | 7.90 d (8.82) | 121.0 | 3a/3b'''' | 2'''', 4a/4b'''' |
| | 5'''' | — | 143.0 | — | — |
| 6''''' | | 4-nitro-benzoic acid | | | |
| | 1''''' | — | 166.5 | — | — |
| | 2''''' | — | 141.5 | — | — |
| | 3a/3b''''' | 8.16 d (8.74) | 129.8 | 4a/4b''''' | 1''''', 3a/3b''''', 5''''' |
| | 4a/4b''''' | 8.39 d (8.78) | 124.4 | 3a/3b''''' | 2''''', 4a/4b''''' |
| | 5''''' | — | 151.0 | — | — |

45

Cystobactamide 819-1:

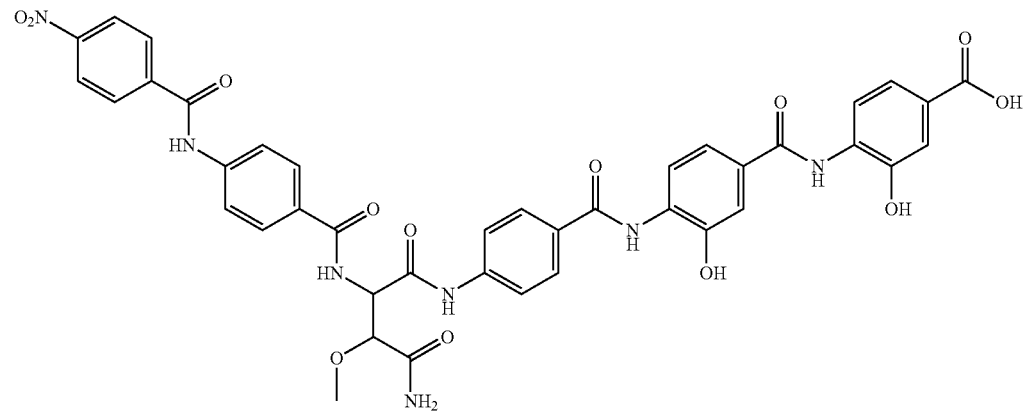

Chemical Formula: $C_{40}H_{33}N_7O_{13}$
Exact Mass: 819.2136

| Fragment/ion | Observed |
|---|---|
| 269.0562 | 269.0552 |
| 413.1097 | 413.1083 |
| 532.1468 | 532.1456 |
| 667.1789 | 667.1429 |
| 820.2209 | 820.2211 |
Cystobactamide 845-2:
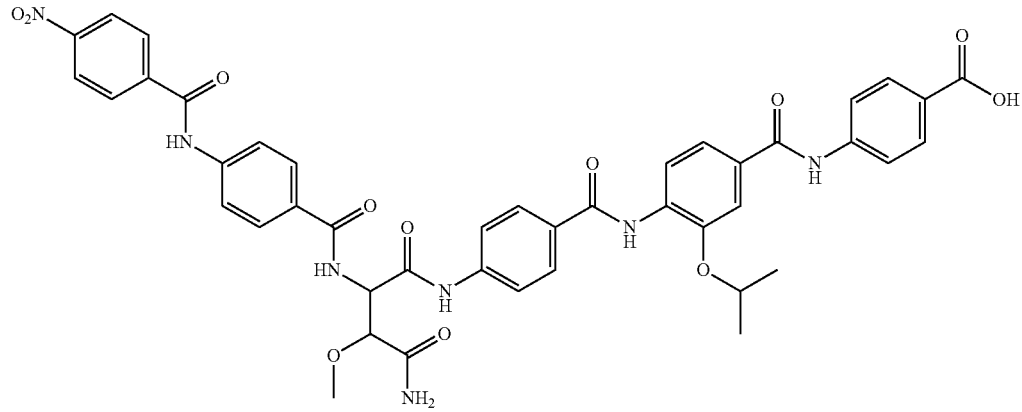
Chemical Formula: $C_{43}H_{39}N_7O_{12}$
Exact Mass: 845.2657
| Fragment/ion | Observed |
|---|---|
| 269.0562 | 269.0556 |
| 413.1097 | 413.1074 |
| 532.1468 | 532.1458 |
| 709.2258 | 709.2235 |
| 846.2729 | 846.2737 |
Cystobactamide 846-1:
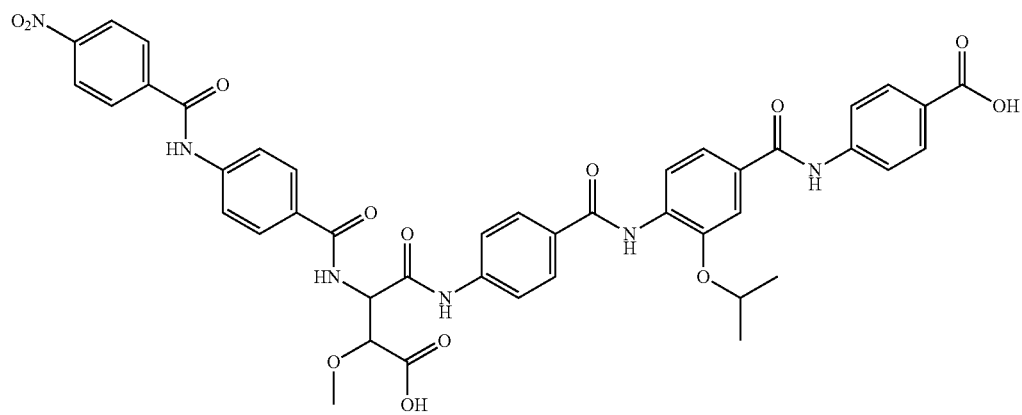
Chemical Formula: $C_{43}H_{38}N_6O_{13}$
Exact Mass: 846.8497

| Fragment/ion | Observed |
|---|---|
| 269.0562 | 269.0548 |
| 414.0937 | 414.0922 |
| 533.1309 | 533.1294 |
| 710.2098 | 710.2033 |
| 847.2570 | 847.2568 |
Cystobactamide 861-1:
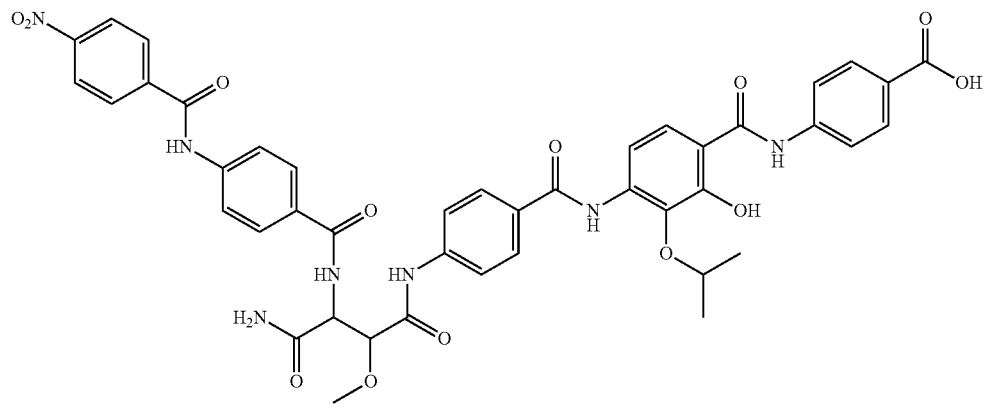
Chemical Formula: $C_{43}H_{39}N_7O_{13}$
Exact Mass: 861.2606
| Fragment/ion | Observed |
|---|---|
| 269.0562 | 269.0558 |
| 413.1097 | not observed |
| 532.1468 | 532.1456 |
| 725.2207 | 725.2187 |
| 862.2679 | 862.2701 |
Cystobactamide 862-1:
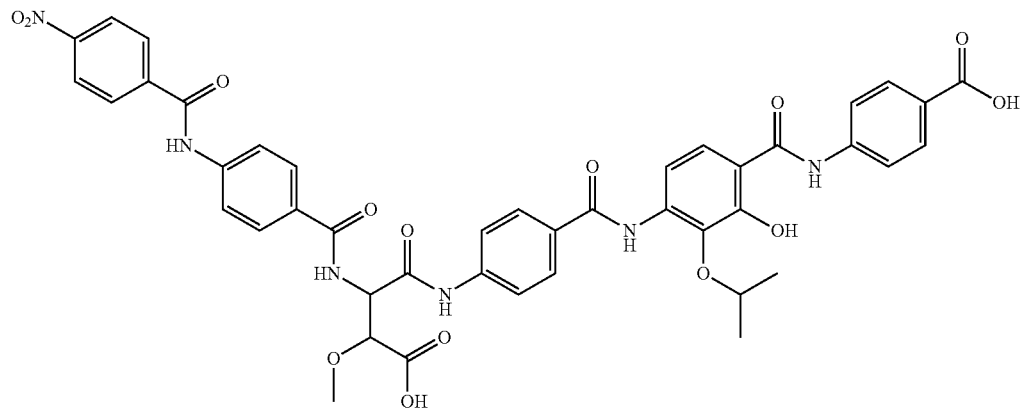
Chemical Formula: $C_{43}H_{38}N_6O_{14}$
Exact Mass: 862.2446

| Fragment/ion | Observed |
|---|---|
| 269.0562 | 269.0551 |
| 414.0937 | 414.0922 |
| 533.1309 | 533.1295 |
| 726.2047 | 726.2095 |
| 863.2519 | 863.2518 |
Cystobactamide 862-2:
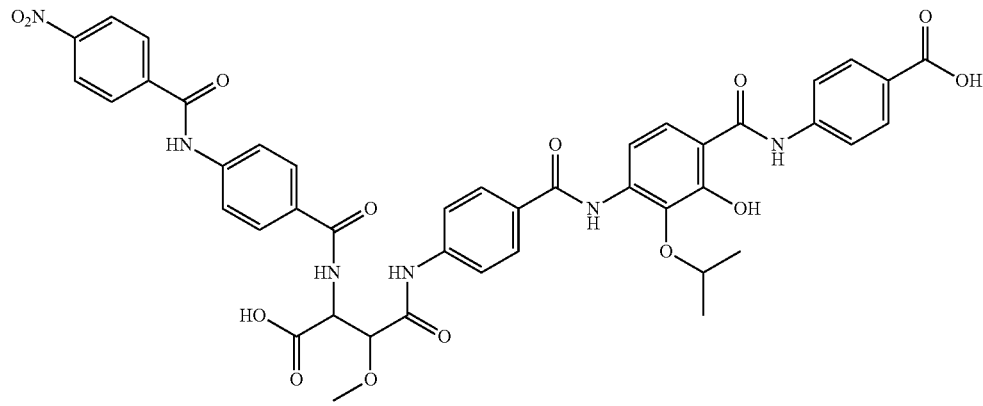
Chemical Formula: C$_{43}$H$_{38}$N$_6$O$_{14}$
Exact Mass: 862.2446
| Fragment/ion | Observed |
|---|---|
| 269.0562 | 269.0555 |
| 414.0937 | not observed |
| 533.1309 | 533.1288 |
| 726.2047 | 726.1993 |
| 863.2519 | 863.2525 |
Cystobactamide 891-1:
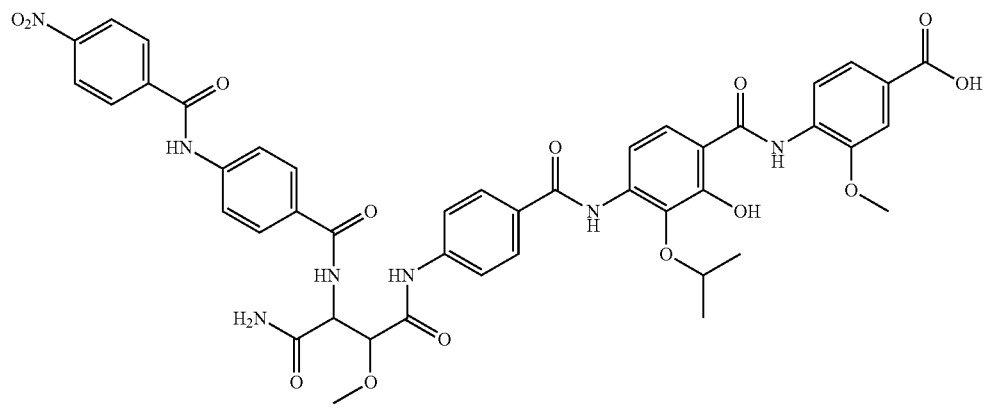
Chemical Formula: C$_{44}$H$_{41}$N$_7$O$_{14}$
Exact Mass: 891.2711

| Fragment/ion | Observed |
|---|---|
| 269.0562 | 269.0558 |
| 413.1097 | not observed |
| 532.1468 | 532.1456 |
| 725.2207 | 725.2143 |
| 892.2784 | 892.2798 |
Cystobactamide 903-1:
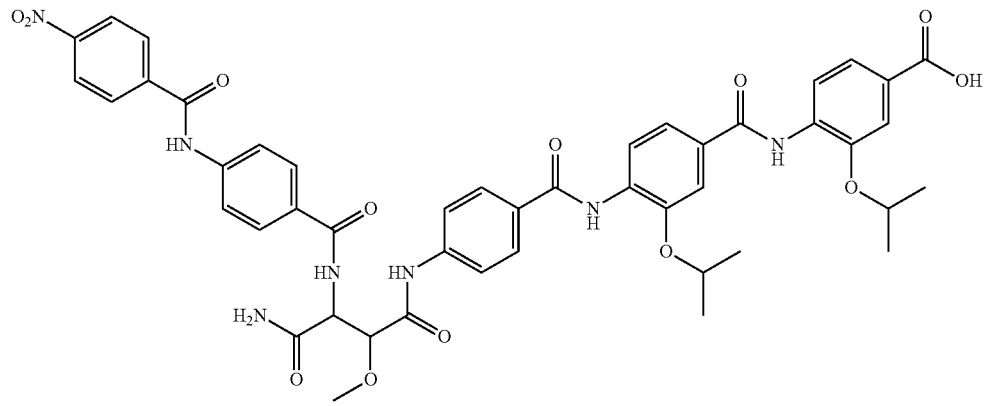
Chemical Formula: $C_{46}H_{45}N_7O_{13}$
Exact Mass: 903.3075
| Fragment/ion | Observed |
|---|---|
| 269.0562 | 269.0669 |
| 413.1097 | not observed |
| 532.1468 | 532.1546 |
| 709.2258 | 709.2294 |
| 904.3148 | 904.3230 |
Cystobactamide 903-2:
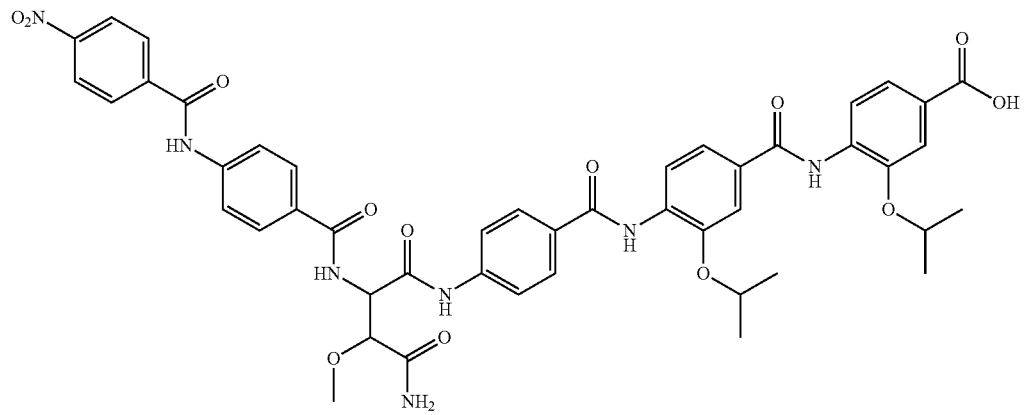
Chemical Formula: $C_{46}H_{45}N_7O_{13}$
Exact Mass: 903.3075

| Fragment/ion | Observed |
| --- | --- |
| 269.0562 | 269.0675 |
| 413.1097 | 413.1189 |
| 532.1468 | 532.1549 |
| 709.2258 | 709.2316 |
| 904.3148 | 904.3216 |
Cystobactamide 905-1:
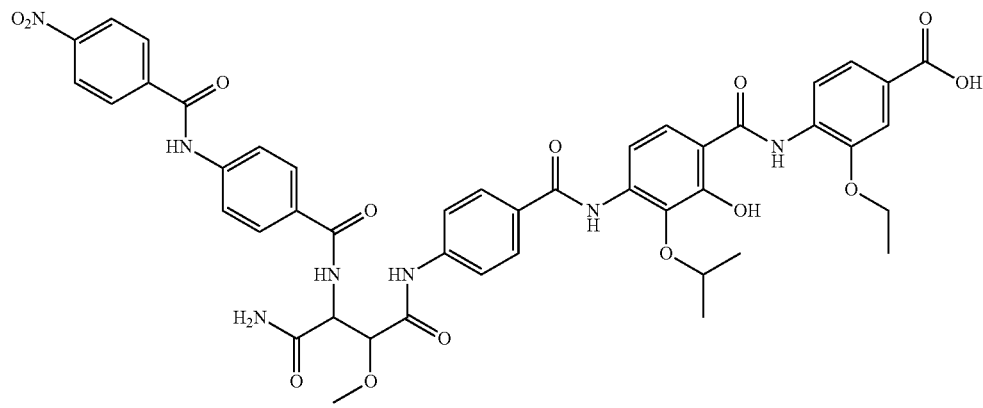
Chemical Formula: $C_{45}H_{43}N_7O_{14}$
Exact Mass: 905.2868
| Fragment/ion | Observed |
| --- | --- |
| 269.0562 | 269.0677 |
| 413.1097 | not observed |
| 532.1468 | 532.1538 |
| 725.2207 | 725.2274 |
| 906.2941 | 906.3020 |
Cystobactamide 905-2:
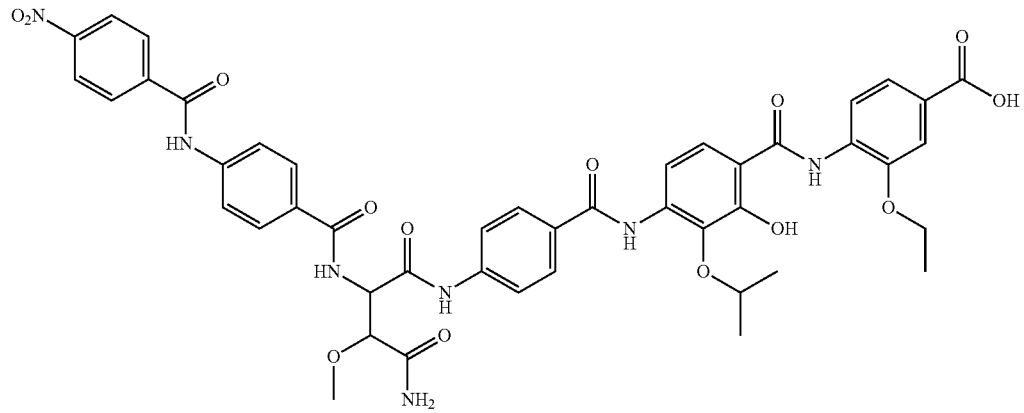
Chemical Formula: $C_{45}H_{43}N_7O_{14}$
Exact Mass: 905.2868

| Fragment/ion | Observed |
|---|---|
| 269.0562 | 269.0555 |
| 413.1097 | 413.1088 |
| 532.1468 | 532.1447 |
| 725.2207 | 725.2191 |
| 906.2941 | 906.2952 |
Cystobactamide 920-1:
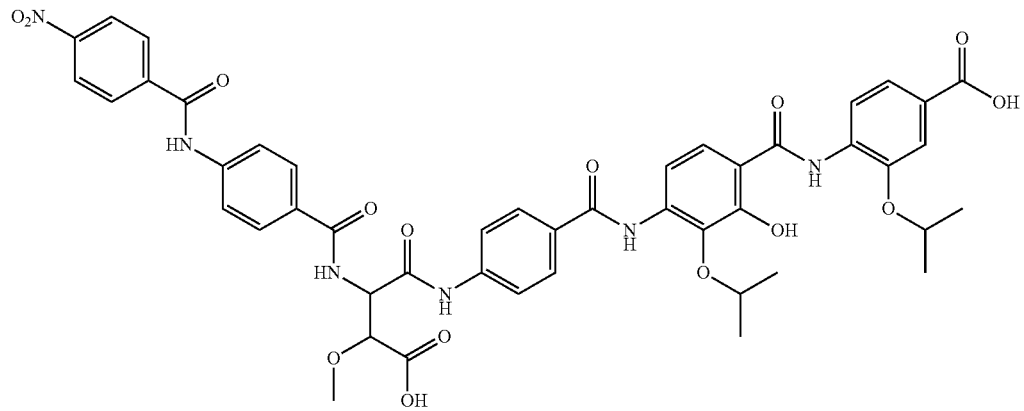
Chemical Formula: $C_{46}H_{44}N_6O_{15}$
Exact Mass: 920.2865
| Fragment/ion | Observed |
|---|---|
| 269.0562 | 269.0556 |
| 414.0937 | 414.0933 |
| 533.1309 | 533.1298 |
| 726.2047 | 726.2034 |
| 921.2937 | 921.2962 |
Cystobactamide 933-1:
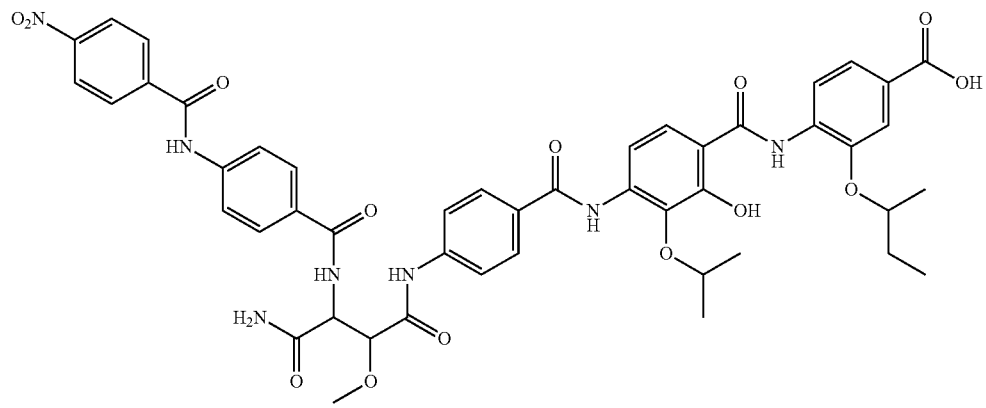
Chemical Formula: $C_{47}H_{47}N_7O_{14}$
Exact Mass: 933.3181

| Fragment/ion | Observed |
|---|---|
| 269.0562 | 269.0559 |
| 413.1097 | not observed |
| 532.1468 | 532.1459 |
| 725.2207 | 725.2197 |
| 934.3254 | 934.3265 |
Cystobactamide 933-2:
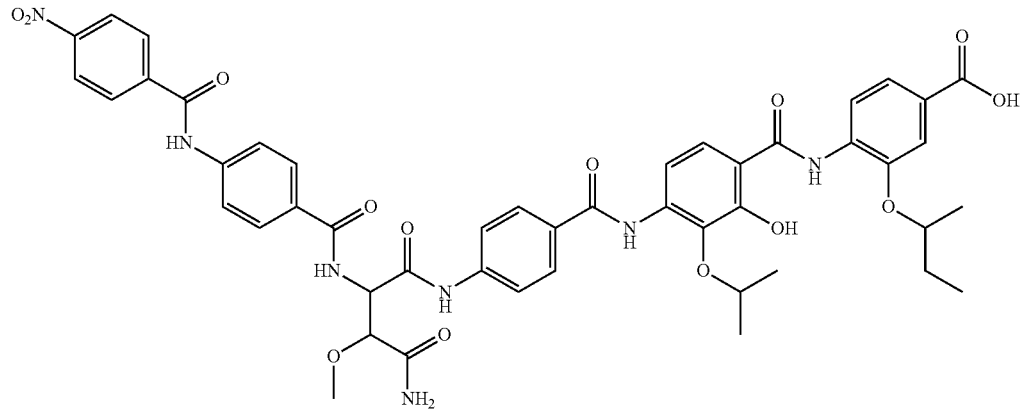
Chemical Formula: $C_{47}H_{47}N_7O_{14}$
Exact Mass: 933.3181
| Fragment/ion | Observed |
|---|---|
| 269.0562 | 269.0557 |
| 413.1097 | 413.1092 |
| 532.1468 | 532.1454 |
| 725.2207 | 725.2175 |
| 934.3254 | 934.3275 |
Cystobactamide 934-1:
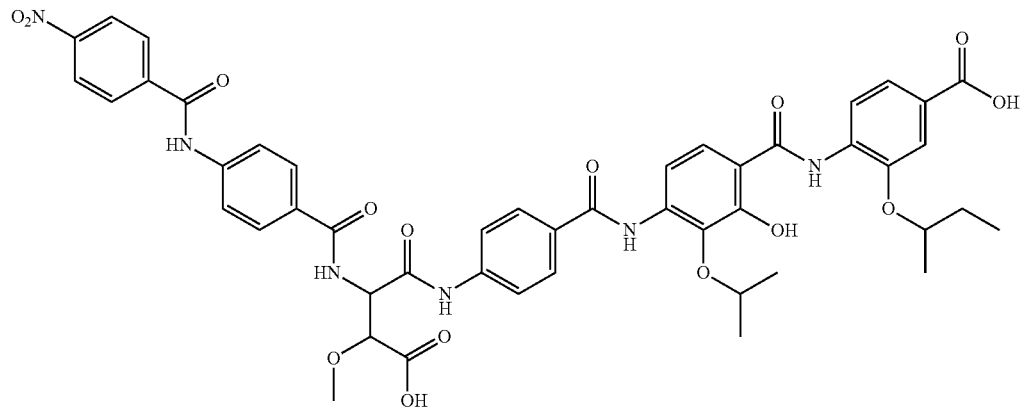
Chemical Formula: $C_{47}H_{46}N_6O_{15}$
Exact Mass: 934.3021

| Fragment/ion | Observed |
|---|---|
| 269.0562 | 269.0551 |
| 414.0937 | 414.0930 |
| 533.1309 | 533.1289 |
| 726.2047 | 726.2076 |
| 935.3094 | 935.3103 |
Cystobactamide 934-2
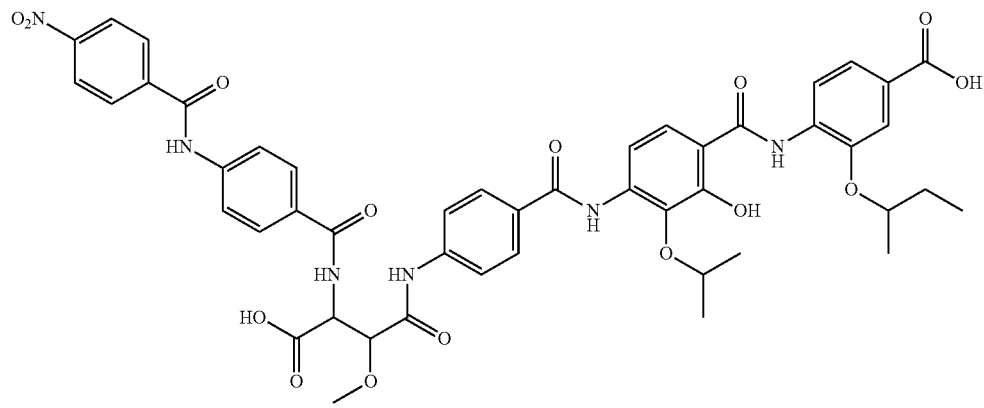
Chemical Formula: $C_{47}H_{46}N_6O_{15}$
Exact Mass: 934.3021
| Fragment/ion | Observed |
|---|---|
| 269.0562 | 269.0558 |
| 414.0937 | not observed |
| 533.1309 | 533.1296 |
| 726.2047 | 726.2019 |
| 935.3094 | 935.3116 |
Cystobactamide 919-2:
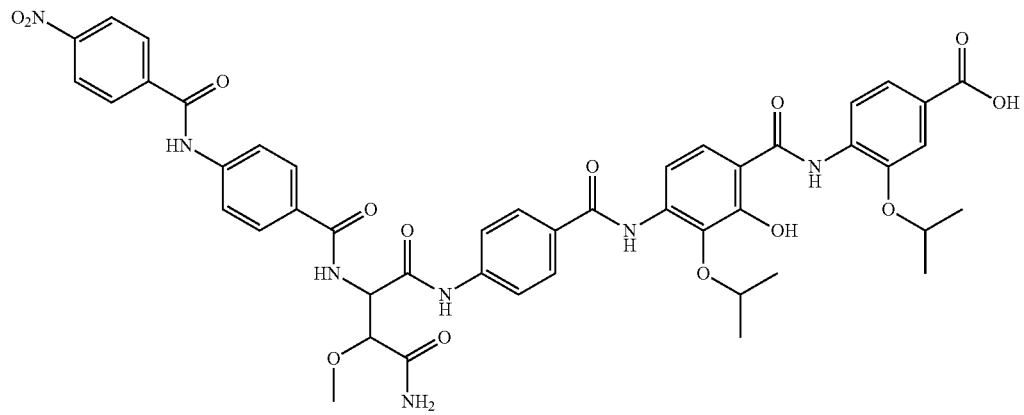
Chemical Formula: $C_{46}H_{45}N_7O_{14}$
Exact Mass: 919.3024

HRMS (ESI) for $C_{46}H_{46}N_7O_{14}$ [M+H]$^+$: calculated 920.3103. found 920.3106.

NMR data of Cystobactamide 919-2 in MeOH-d$_4$:

| pos. | $\delta_H$, mult (J in Hz) | $\delta_C$* | COSY | HMBC |
|---|---|---|---|---|
| 4-amino-3-isopropoxy-benzoic acid | | | | |
| 1 | — | 172.9 | — | — |
| 2 | — | 132.4 | — | — |
| 3 | 7.68 s | 115.1 | 7 | 1, 5, 7 |
| 4 | — | 148.1 | — | — |
| 5 | — | 132.3 | — | — |
| 6 | 8.37 d (8.9) | 120.9 | 7 | 2, 4 |
| 7 | 7.63 broad d (8.5) | 123.3 | 3, 6 | 1, 5, 6 |
| 8 | 4.77 m | 72.8 | 9a/9b | 4, 9a/9b |
| 9a/9b | 1.45 d (6.1) | 22.2 | 8 | 8 |
| 4-amino-2-hydroxy-3-isopropoxy-benzoic acid | | | | |
| 1' | — | 166.9 | — | — |
| 2' | — | 116.6 | — | — |
| 3' | — | 153.4 | — | — |
| 4' | — | 138.6 | — | — |
| 5' | — | 137.2 | — | — |
| 6' | 7.74 m | 114.2 | 7' | 2', 4' |
| 7' | 7.76 d (8.9) | 124.9 | 6' | 1', 3', 5' |
| 8' | 4.57 m | 76.8 | 9a/9b' | 4', 9a/9b' |
| 9a/9b' | 1.35 d (6.2) | 22.5 | 8' | 8' |
| 4-amino-benzoic acid | | | | |
| 1" | — | 166.9 | — | — |
| 2" | — | 130.6 | — | — |
| 3a/3b" | 7.96 d (8.7) | 129.2 | 4a/4b" | 1", 3a/3b", 5" |
| 4a/4b" | 7.84 d (8.7) | 120.7 | 3a/3b" | 2", 4a/4b" |
| 5" | — | 143.1 | — | — |
| asparagine | | | | |
| 1''' | — | 169.6 | — | — |
| 2''' | 5.08 d (7.4) | 57.2 | 3''' | 1''', 4''', 3''', 1'''' |
| 3''' | 4.18 d (7.4) | 82.1 | 2''' | 1''', 2''', 4''' |
| 4''' | — | 174.5 | — | — |
| 5''' | 3.50 s | 59.1 | — | 3''' |
| 4-amino-benzoic acid | | | | |
| 1'''' | — | 169.0 | — | — |
| 2'''' | — | 130.4 | — | — |
| 3a/3b'''' | 7.92 d (8.7) | 129.3 | 4a/4b'''' | 1'''', 3a/3b'''', 5'''' |
| 4a/4b'''' | 7.89 d (8.8) | 121.0 | 3a/3b'''' | 2'''', 4a/4b'''' |
| 5'''' | — | 143.1 | — | — |
| 4-nitro-benzoic acid | | | | |
| 1''''' | — | 166.5 | — | — |
| 2''''' | — | 141.6 | — | — |
| 3a/3b''''' | 8.16 d (8.8) | 129.9 | 4a/4b''''' | 1''''', 3a/3b''''', 5''''' |
| 4a/4b''''' | 8.38 d (8.7) | 124.4 | 3a/3b''''' | 2''''', 4a/4b''''', 5''''' |
| 5''''' | — | 151.0 | — | — |

NMR data of cystobactamid 919-2 in DMSO-d$_6$.

| pos. | $\delta_H$, mult (J in Hz) | $\delta_C$* | COSY correlations | HMBC correlations | ROESY correlations |
|---|---|---|---|---|---|
| 4-amino-3-isopropoxy-benzoic acid* | | | | | |
| 1 | — | — | — | — | — |
| 2 | — | — | — | — | — |
| 3 | — | — | — | — | — |
| 4 | — | — | — | — | — |
| 5 | — | — | — | — | — |
| 6 | — | — | — | — | — |
| 7 | — | — | — | — | — |
| 8 | — | — | — | — | — |
| 9a/9b | — | — | — | — | — |
| 4-amino-2-hydroxy-3-isopropoxy-benzoic acid* | | | | | |
| 1' | — | — | — | — | — |
| 2' | — | — | — | — | — |
| 3' | — | — | — | — | — |
| 4' | — | — | — | — | — |
| 5' | — | — | — | — | — |
| 6' | — | — | — | — | — |
| 7' | — | — | — | — | — |
| 8' | — | — | — | — | — |
| 9a/9b | — | — | — | — | — |
| 4-amino-benzoic acid | | | | | |
| 1" | — | 165.7 | — | — | — |
| 2" | — | 128.6 | — | — | — |
| 3a/3b" | 7.95 m | 128.1 | 4a/4b" | 1", 3a/3b", 5" | — |
| 4a/4b" | 7.83 d (8.7) | 118.7 | 3a/3b" | 2", 4a/4b" | — |
| 5" | — | 141.7 | — | — | — |
| 6" | 10.56 s | — | — | 4a/4b", 1''' | 4a/4b", 2''' |
| asparagine | | | | | |
| 1''' | — | 168.4 | — | — | — |
| 2''' | 4.92 m | 55.4 | 3''' | 1''', 3''', 4''', 1'''', | — |
| 3''' | 4.09 d (7.9) | 79.8 | 2''' | 1''', 2''', 4''', 5''', | — |
| 4''' | — | 170.6 | — | — | — |
| 5''' | 3.31 s | 57.4 | — | 3''' | — |
| 6''' | 7.48 s; 7.55 s | — | 6''' | 3''', 4''' | 3''' |
| 7''' | 8.46 d (8.3) | — | 2''' | 2''', 1'''' | 3''' |
| 4-amino-benzoic acid | | | | | |
| 1'''' | — | 165.2 | — | — | — |
| 2'''' | — | 128.7 | — | — | — |
| 3a/3b'''' | 7.89 m | 128.1 | 4a/4b'''' | 1'''', 3a/3b'''', 5'''' | — |
| 4a/4b'''' | 7.91 m | 119.4 | 3a/3b'''' | 2'''', 4a/4b'''' | — |
| 5'''' | — | 141.4 | — | — | — |
| 6'''' | 10.81 s | — | — | 4a/4b'''', 5'''', 1''''' | 4a/4b'''', 3a/3b'''' |
| 4-nitro-benzoic acid | | | | | |
| 1''''' | — | 164.0 | — | — | — |
| 2''''' | — | 140.0 | — | — | — |
| 3a/3b''''' | 8.21 d (8.8) | 129.2 | 4a/4b''''' | 1''''', 3a/3b''''', 5''''' | — |
| 4a/4b''''' | 8.39 d (8.7) | 123.3 | 3a/3b''''' | 2''''', 4a/4b''''', 5''''' | — |
| 5''''' | — | 148.9 | — | — | — |

*signals corresponding to these units could not be assigned due to signal broadening effects in NMR spectra in DMSO-$d_6$: see also section "structure elucidation" and FIGS. S42-S45.

Figure 2:
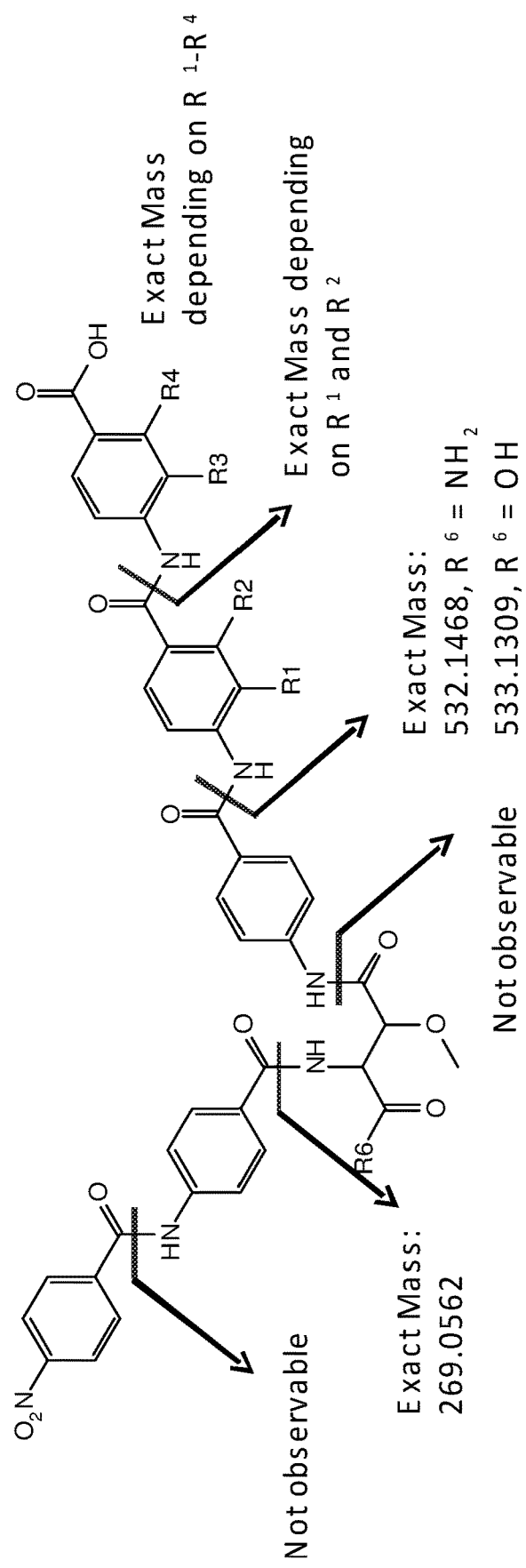

Cystobactamides containing the methoxy-asparagin (or aspartate) fragment as in normal peptides show a 413(414)-fragment in their mass spectra (FIG. 1). Cystobactamides which contain the iso-aminoacid do not show this 413(414)-fragment when methoxy-asparigin (aspartate) is present (FIG. 2). Based on the presence of this fragment in the mass spectra of the Cystobactamides the presence of iso- and non-iso-aminoacids can be elucidated.

2. Biological Evaluation of Cystobactamides

Antibacterial Activity

Cystobactamides (Cys) 919-2, 920-1, 934-2, 935-2, 891-2 and 905-2 were evaluated together with already described derivatives (861-2, 877-2, 920-2) against a selected set of Gram-negative bacteria. Derivatives 861-2, 877-2, 919-1 and 920-2 correspond to Cystobactamides F, H, A and B described in WO 2015/003816. MIC values are given in μg/ml; Ciprofloxacin (CP) was used as reference.

| | Cys 920-2 (B) | Cys 861-2 (F) | Cys 877-2 (H) | Cys 891-2 | Cys 905-2 |
|---|---|---|---|---|---|
| A. baumannii DSM-30008 | >64 | 0.5 | >64 | — | 64 |
| C. freundii DSM-30039 | >64 | 0.06 | 2 | — | 8 |
| E. coli DSM-1116 | >64 | 0.13 | 4 | 1 | 8 |

| | | | | | |
|---|---|---|---|---|---|
| E. coli DSM-26863 (tolC3) | 64 | 0.06 | 1 | 1 | 2 |
| E. coli JW0401-1 (WT) | — | 0.25 | — | — | — |
| E. coli Δtsx | — | 0.25 | — | — | — |
| E. coli WT | >64 | 0.13 | 2 | — | 4 |
| E. coli WT-3 [gyrA(S83L, D87G)] | >64 | 0.5 | >64 | — | >64 |
| E. coli WT-III [marRΔ74bp] | >64 | 0.5 | >64 | 4 | >64 |
| P. aeruginosa DSM-24600 (ESBL) | >64 | 1 | 64 | — | >64 |
| P. vulgaris DSM-2140 | >64 | 0.25 | 4 | — | 32 |

| | Cys 919-2 | Cys 920-1 | Cys 934-2 | Cys 935-2 | CP |
|---|---|---|---|---|---|
| A. baumannii DSM-30008 | 8 | >64 | >64 | 2 | 0.8 |
| C. freundii DSM-30039 | 1 | >64 | >64 | 1 | 0.003 |
| E. coli DSM-1116 | 0.5 | >64 | >64 | 0.5 | 0.01 |
| E. coli DSM-26863 (tolC3) | 0.25 | 64 | 32 | 0.25 | ≤0.003 |
| E. coli JW0401-1 (WT) | 1 | — | — | — | — |
| E. coli Δtsx | 1 | — | — | — | — |
| E. coli WT | 0.5 | >64 | >64 | 0.5 | 0.013 |
| E. coli WT-3 [gyrA(S83L, D87G)] | 64 | >64 | >64 | 2 | 0.8 |
| E. coli WT-III [marRΔ74bp] | >64 | >64 | >64 | 2 | 0.1 |
| P. aeruginosa DSM-24600 (ESBL) | 64 | >64 | >64 | 8 | 3.2 |
| P. vulgaris DSM-2140 | 4 | >64 | >64 | 1 | 0.01 |

Cystobactamides 919-2 and 891-2 were tested together with already described derivatives 861-2 (F) and 919-1 (A) on a larger panel of microorganisms and the CHO-K1 cell line.

| | Cys 861-2 (F) | Cys 919-1 (A) | Cys 891-2 | Cys 919-2 | CP |
|---|---|---|---|---|---|
| Acinetobacter baumannii DSM-30008 | 0.5 | >64 | — | 8 | 0.2-0.4 |
| Burkholderia cenocepacia DSM-16553 | — | >64 | — | >64 | >6.4 |
| Chromobacterium violaceum DSM-30191 | — | >64 | — | 15 | 0.006-0.013 |
| Citrobacter freundii DSM-30039 | 0.06 | — | — | 1 | 0.003 |
| Escherichia coli WT | 0.125 | 16 | — | 0.5 | 0.013 |
| Escherichia coli MI [gyrA(S83L)] | — | >64 | — | 4 | 0.4-0.8 |
| Escherichia coli WT-3.2 [gyrA(D87G)] | — | >64 | — | 4 | 0.4 |
| Escherichia coli WT-3 [gyrA(S83L, D87G)] | 0.5 | >64 | — | 16-32 | 0.8-1.6 |
| Escherichia coli WT-4 M2.1 [parC(S80I)] | — | 32 | — | 1 | 0.013 |
| Escherichia coli MI-4 [gyrA(S83L), parC(S80I)] | — | >64 | — | 2-4 | 0.8 |
| Escherichia coli WTIII (marRΔ74bp) | 0.5 | >64 | 4 | 64 | 0.1 |
| Escherichia coli DSM-1116 | 0.4 | 16-32 | 1 | 1 | 0.013 |
| Escherichia coli DSM-12242 (NAL$^R$) | — | 32 | — | 1-2 | 0.05 |
| Escherichia coli DSM-26863 (tolC3) | 0.4 | 8 | 1 | 0.5-1 | 0.003 |
| Escherichia coli (TolC-deficient) | 0.06 | — | — | — | 0.01 |
| Escherichia coli ATCC35218 | — | 16-32 | — | 1 | 0.013 |
| Escherichia coli ATCC25922 | — | 8 | — | 0.5 | 0.006 |
| Enterobacter aerogenes DSM-30053 | — | >64 | — | >64 | 0.1-0.2 |
| Enterobacter cloacae DSM-30054 | 64 | — | — | >64 | 0.01 |
| Klebsiella pneumoniae DSM-30104 | — | >64 | — | >64 | 0.025 |
| Proteus vulgaris DSM-2140 | 0.25 | — | — | 4 | 0.01 |

| | Cys 861-2 (F) | Cys 919-1 (A) | Cys 891-2 | Cys 919-2 | CP |
|---|---|---|---|---|---|
| Pseudomonas aeruginosa PA14 | 2 | >64 | 8 | >64 | 0.1 |
| Pseudomonas aeruginosa ATCC27853 | 4 | >64 | — | >64 | 0.1-0.2 |
| Pseudomonas aeruginosa DSM-24599 | 2 | — | — | >64 | >6.4 |
| Pseudomonas aeruginosa DSM-24600 (ESBL) | 1 | — | — | 64 | 3.2 |
| Pseudomonas aeruginosa DSM-46316 (ESBL) | 2 | — | — | >64 | 0.1 |
| Serratia marcescens DSM-30121 | 64 | — | — | >64 | 0.1 |
| Mycobacterium smegmatis ATCC700084 | — | >64 | — | >64 | 0.2-0.4 |
| Bacillus subtilis DSM-10 | — | 4 | — | 0.1 | 0.1 |
| Enterococcus faecalis ATCC29212 | — | 4-8 | — | 0.1 | 0.8 |
| Enterococcus faecium DSM-20477 | 0.5 | — | — | 0.25 | >6.4 |
| Micrococcus luteus DSM-1790 | — | 16 | — | 0.1-0.2 | 0.8-1.6 |
| Staphylococcus aureus ATCC29213 | — | 32 | — | 0.1 | 0.05-0.1 |
| Staphylococcus epidermidis DSM-28765 | 0.5 | — | — | 0.25 | 0.2 |
| Streptococcus pneumoniae DSM-20566 | — | 16 | — | 0.1 | 0.8-1.6 |
| Candida albicans DSM-1665 | — | >64 | — | >64 | >6.4 |
| Pichia anomala DSM-6766 | — | >64 | — | >64 | >6.4 |
| CHO-K1 (Chinese hamster ovary cell line)* | >100 | >100 | ca. 50 | ca. 50 | — |

MIC values are given in µg/ml;
*IC$_{50}$ in µM;
Ciprofloxacin (CP) was used as reference Frequency of Resistance The frequency of resistance was determined using E. coli DSM-1116 at the 4-fold MIC for Cystobactamides 861-2 and 919-2 as $10^{-7}$ to $10^{-8}$.

In Vitro Activity

The activity on E. coli and P. aeruginosa gyrase DNA supercoiling (sc) activity was determined for cystobactamide 861-2 in comparison to cystobactamide 919-2 and Ciprofloxacin (CP).

| IC$_{50}$ [µM] | Cys861-2 | Cys919-2 | CP |
|---|---|---|---|
| Ec gyrase (sc) | 0.28 | 0.67 | 0.40 |
| Pa gyrase (sc) | 0.18 | 0.34 | 0.48 |

Genotoxicity

No detectable genotoxic effect was observed in a micronucleus formation assay with the CHO-K1 cell line for cystobactamides 861-2, 919-2 and ciprofloxacin at 20 µg/ml. Mitomycin C (100 ng/ml) was used as positive control. All experiments have been performed in triplicates and microscopic images of stained nuclei were evaluated. Micronucleus formation was clearly observed in mitomycin C-treated CHO-K1 cells but not in the untreated control, ciprofloxacin-, and cystobactamid-treated cells.

Materials and Methods

MIC Determination.

Indicator strains used in susceptibility assays were either part of our strain collection or purchased from the German Collection of Microorgansims and Cell Cultures (DSMZ) or from the American Type Culture Collection (ATCC). E. coli strain WT and corresponding *E. coli* mutants were kindly provided by Prof. Dr. P. Heisig, Pharmaceutical Biology and Microbiology, University of Hamburg. *E. coli* strains JW0401-1 (WT) and Δtsx were obtained from the CGSC collection.

MIC values were determined in standardized microdilution assays. Overnight cultures were diluted in the appropriate growth medium to achieve an inoculum of $10^4$-$10^6$ cfu/mL. Yeasts were grown in Myc medium (1% phytone peptone, 1% glucose, 50 mM HEPES, pH 7.0), *S. pneumonia* and *Enterococcus* spp. in tryptic soy broth (TSB: 1.7% peptone casein, 0.3% peptone soymeal, 0.25% glucose, 0.5% NaCl, 0.25% $K_2HPO_4$; pH 7.3); *M. smegmatis* in Middlebrook 7H9 medium supplemented with 10% Middlebrook ADC enrichment and 2 ml/l glycerol). All other listed bacteria were grown in Müller-Hinton broth (0.2% beef infusion solids, 1.75% casein hydrolysate, 0.15% starch, pH 7.4). Cystobactamides and reference drugs were added directly to the cultures in sterile 96-well plates as duplicates and serial dilutions were prepared. Microorganisms were grown on a microplate shaker (750 rpm, 30-37° C., 18-48 h), except *S. pneumonia*, which was grown at non-shaking conditions (37° C., 5% $CO_2$, 18 h). Growth inhibition was assessed by visual inspection and the MIC was defined as the lowest concentration of compound that inhibited visible growth.

Cytotoxicity.

CHO-K1 cells were obtained from the DSMZ and were cultured under conditions recommended by the depositor. Cells were seeded at $6 \times 10^3$ cells/well of 96-well plates in 180 μl complete medium and treated with compounds in serial dilution after 2 h of equilibration. Each sample was tested in duplicate as well as the internal DMSO control. After 5 d incubation, 20 μl of 5 mg/ml MTT (thiazolyl blue tetrazolium bromide) in PBS was added per well and it was further incubated for 2 h at 37° C. The medium was then discarded and cells were washed with 100 μl PBS before adding 100 μl 2-propanol/10 N HCl (250:1) in order to dissolve formazan granules. The absorbance at 570 nm was measured using a microplate reader (Tecan Infinite M200Pro), and cell viability was expressed as percentage relative to the respective methanol control.

Resistance Rate.

In order to determine the frequency of spontaneous resistance to Cystobactamides, log-phase bacterial cell suspensions were adjusted in Müller-Hinton broth to a final concentration of $10^{10}$ CFU/mL and different volumes were streaked out on replicate agar plates containing cystobactamides at their 4-fold MIC on *E. coli* DSM-1116. In addition, several dilutions of the *E. coli* culture were streaked out on plates containing no antibiotic. After 1 d, frequencies of resistance were determined by dividing the CFUs on cystobactamide-containing plates by the number of CFUs on antibiotic-free plates.

Enzyme Inhibition.

To test the anti-gyrase activity of cystobactamides, commercial *E. coli* and *P. aeruginosa* gyrase supercoiling kits (Inspiralis, Norwich, UK) were used. For standard reactions 0.5 μg relaxed plasmid were mixed with 1 unit gyrase in 1× reaction buffer (see kit manual) and incubated for 30 min at 37° C. The reactions were quenched by the addition of DNA gel loading buffer containing 10% (w/v) SDS. The samples were separated on 1% (w/v) agarose gels and DNA was visualized using EtBr. All natural products stock solutions and dilutions were prepared in 100% DMSO and added to the supercoiling reactions giving a final DMSO concentration of 2% (v/v).

Genotoxicity Studies.

Chinese hamster ovary CHO-K1 cells (ACC-110) were obtained from the DSMZ and were maintained under conditions recommended by the depositor. For genotoxicity studies the cells were seeded at $5 \times 10^3$ cells/well in black 96-well plates with optical bottom and allowed to adhere for 1 d prior to compound addition. CP, cystobactamides and mitomycin C were added to a final concentration of 20 μg/ml (gyrase inhibitors) and 100 ng/ml (mitomycin C). The cells were treated for 48 h, washed twice with phosphate-buffered saline (PBS, pH 7.4) and fixed using AcO/MeOH (1:1, −20° C.) for 10 min at room temperature. After repeated washing with PBS nuclei were stained with 5 μg/mL Hoechst33342 in PBS for 15 min at room temperature protected from light. After washing, the samples were imaged (200× magnification) on an automated microscope (Pathway855, BD Biosciences) with an appropriate filter set for Hoechst. All samples were prepared and analyzed for micronucleus formation as triplicates in two independent experiments.

3. Synthesis of Cystobactamide C Derivatives

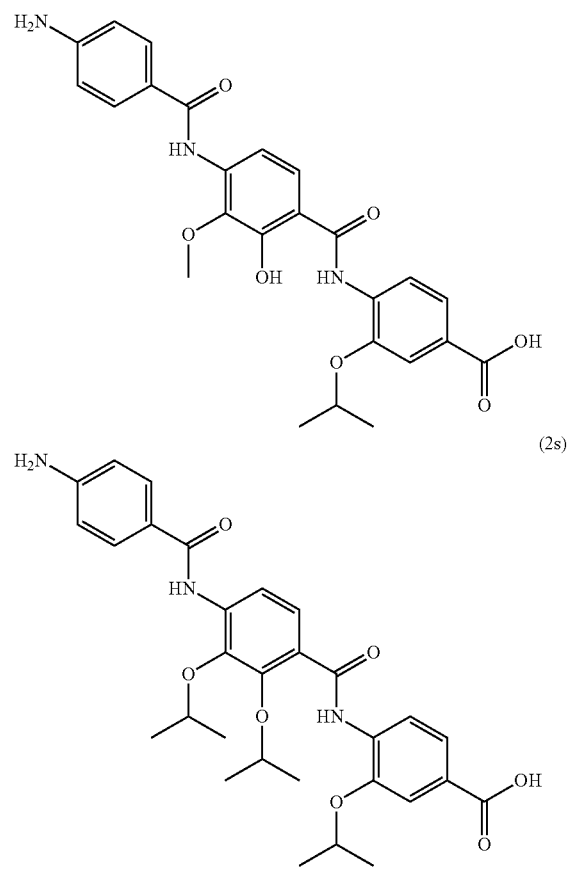

53
-continued (3s)

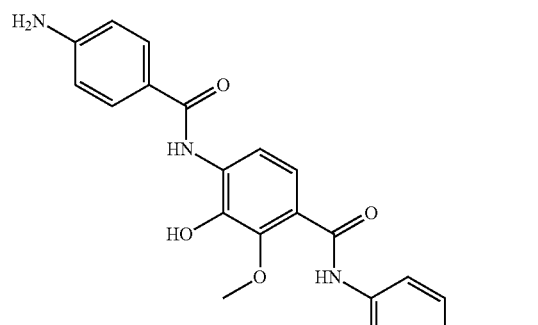

(4s)

3.1 Synthesis of the Different Used Individual Rings

The preparation of the different individual rings that were used during the synthesis of the cystobactamide C derivatives is described here.

Preparation of Ring C

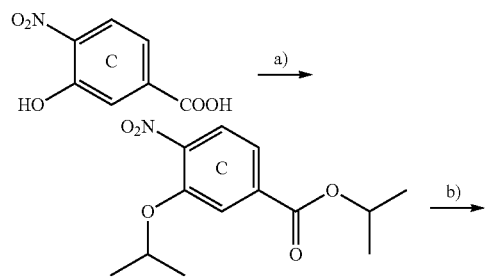

54
-continued

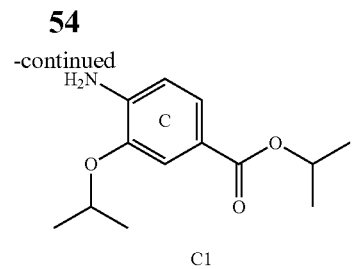

C1 a) BrCH(CH₃)₂, K₂CO₃, DMF, 90° C., overnight; b) Fe, NH₄Cl, EtOH/H₂O, reflux, 2 hours Preparation of Ring B

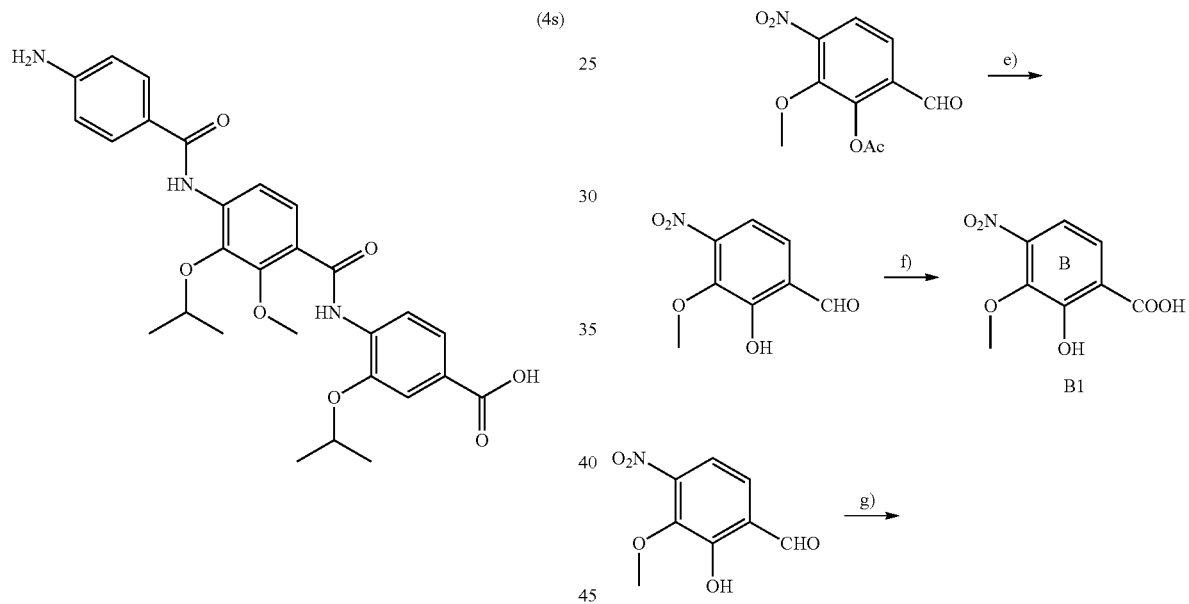

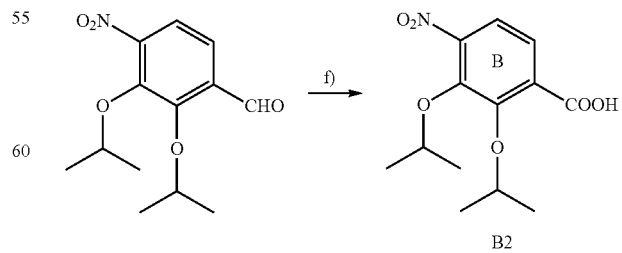

B2 a) BrCH(CH₃)₂, K₂CO₃, DMF, 90° C., overnight; c) AcCl/pyridine; d) KNO₃/TFAA, e) NaOH; f) AgNO₃/NaOH; g) BBr₃, DCM, rt, overnight

3.2 Coupling of Ring B and C to Give the Different Prepared BC Fragments
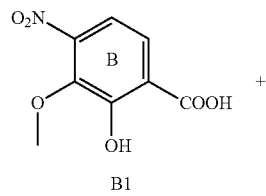
B1
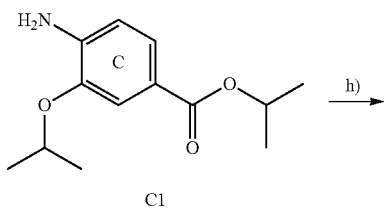
C1
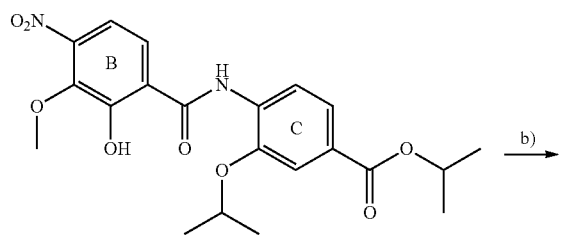
BC1
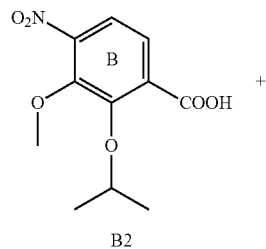
B2
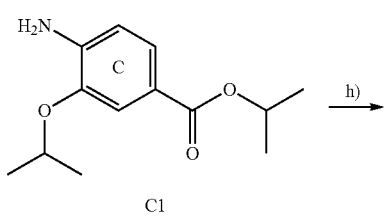
C1
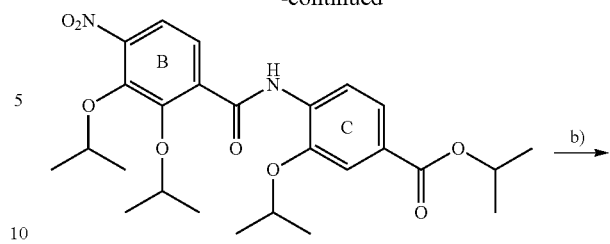
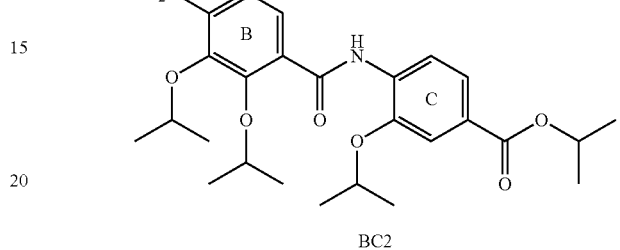
BC2
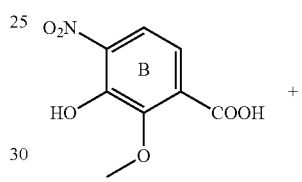
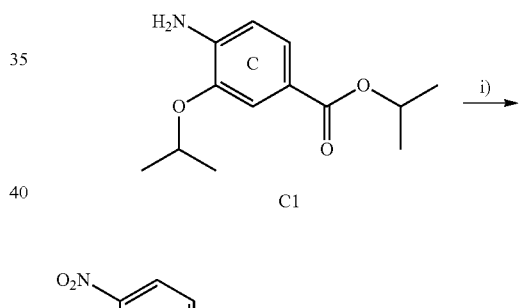
C1
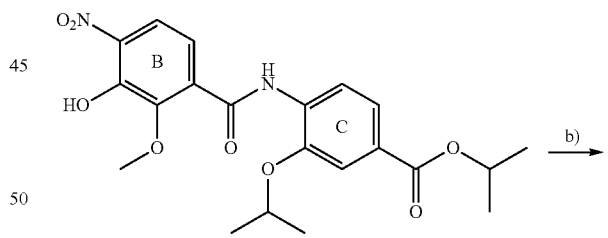
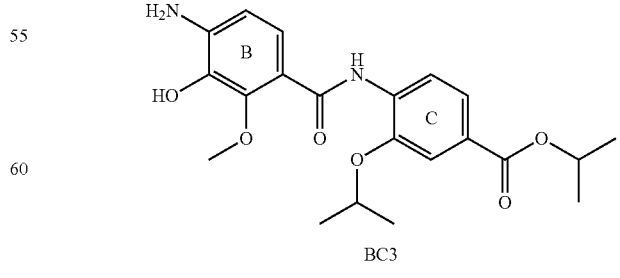
BC3
b) Fe, NH₄Cl, EtOH/H₂O, reflux, 2 hours; h) Cl₂PPh₃, CHCl₃; i) PCl₃, CH₂Cl₂, Xylene, 145° C., 2 hours 3.3. Coupling of Ring A with BC Fragments (BC1, BC2, BC3) to Synthesize the Cystobactamide C Derivatives (1s)-(3s)
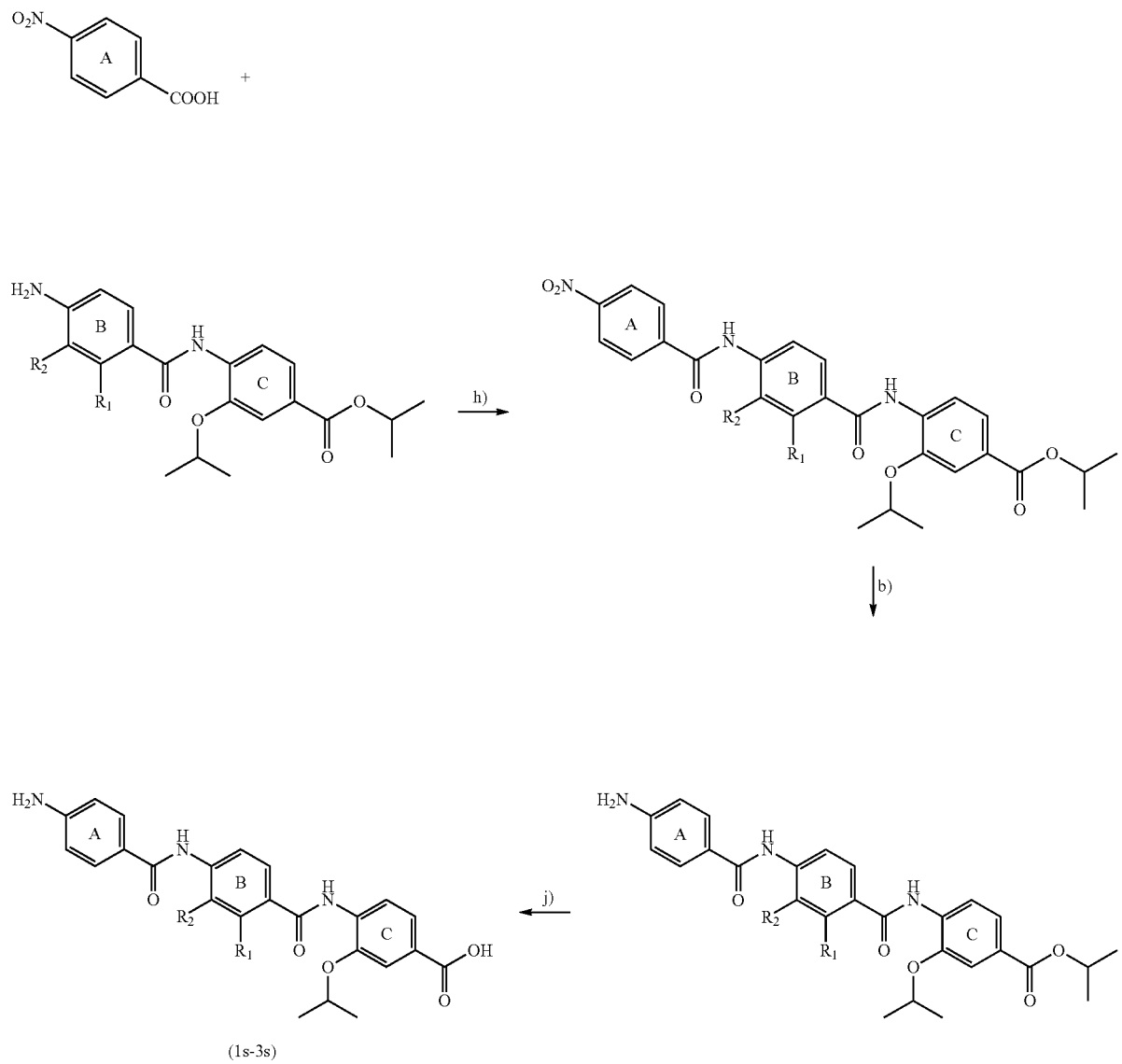
b) Fe, NH₄Cl, EtOH/H₂O, reflux, 2 hours; h) Cl₂PPh₃, CHCl₃; j) NaOH/MeOH, 45° C., overnight;
| Compound | R₁ | R₂ |
|---|---|---|
| (1s) | OH | OMe |
| (2s) | OiPr | OiPr |
| (3s) | OMe | OH |

3.4 Preparation of Compound 4s

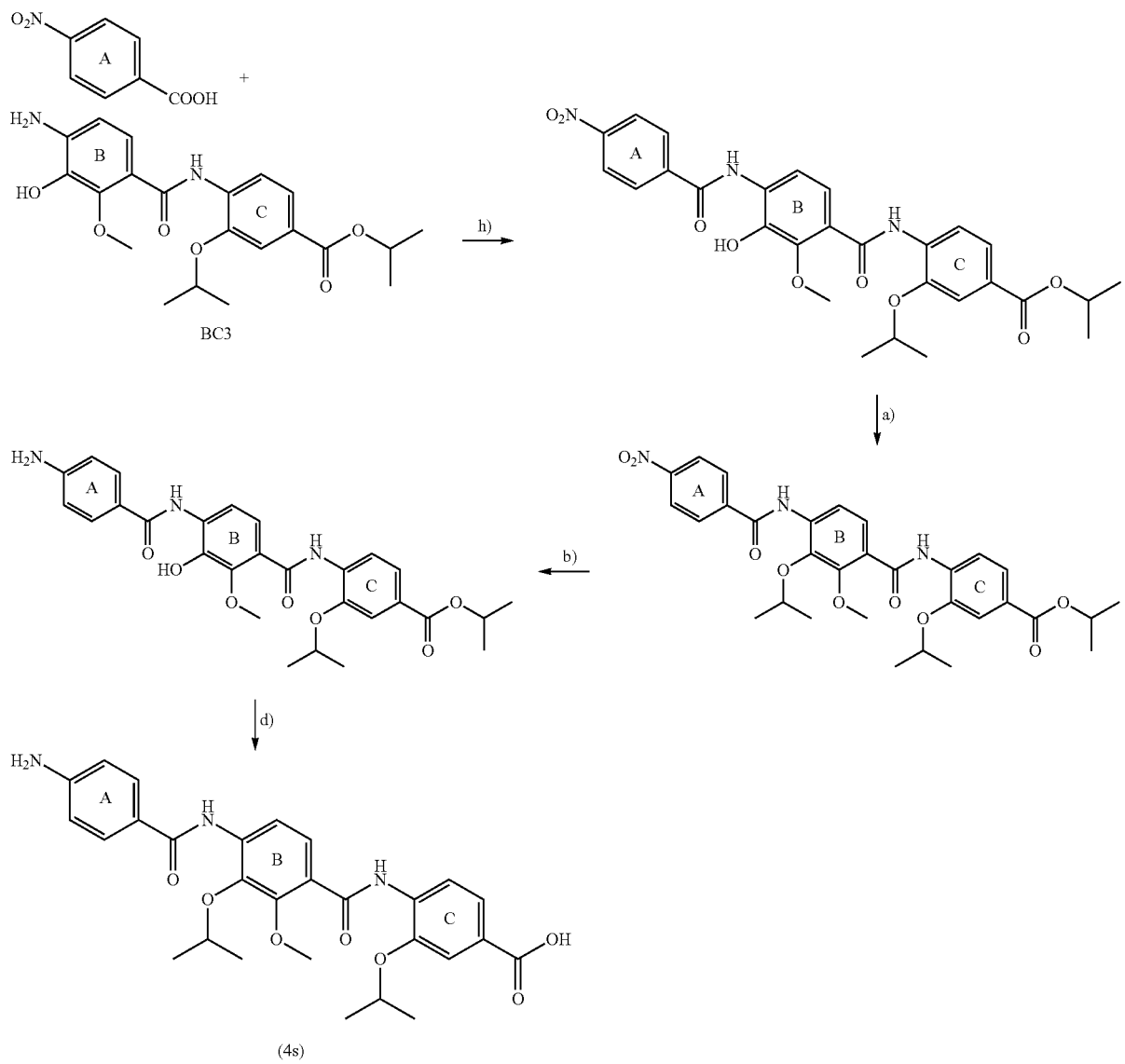

a) BrCH(CH3)2, K2CO3, DMF, 90° C., overnight; b) Fe, NH4Cl, EtOH/H2O, reflux, 2 hours; d) NaOH/MeOH, 45° C., overnight; h) Cl2PPh3, CHCl3

3.5. Experimental

3.5.1. General Experimental Information

Starting materials and solvents were purchased from commercial suppliers, and used without further purification. All chemical yields refer to purified compounds, and not optimized. Reaction progress was monitored using TLC Silica gel 60 $F_{254}$ aluminium sheets, and visualization was accomplished by UV at 254 nm. Flash chromatography was performed using silica gel 60 Å (40-63 μm). Preparative RP-HPLC was carried out on a Waters Corporation setup contains a 2767 sample manager, a 2545 binary gradient module, a 2998 PDA detector and a 3100 electron spray mass spectrometer. Purification was performed using a Waters XBridge column (C18, 150×19 mm, 5 μm), a binary solvent system A and B (A=water with 0.1% formic acid; B=MeCN with 0.1% formic acid) as eluent, a flow rate of 20 mL/min and a gradient of 60% to 95% B in 8 min were applied. Melting points were determined on a Stuart Scientific melting point apparatus SMP3 (Bibby Sterilin, UK), and are uncorrected. NMR spectra were recorded either on Bruker DRX-500 ($^1$H, 500 MHz; $^{13}$C, 126 MHz), or Bruker Fourier 300 ($^1$H, 300 MHz; $^{13}$C, 75 MHz) spectrometer at 300 K. Chemical shifts are recorded as δ values in ppm units by reference to the hydrogenated residues of deuterated solvent as internal standard (CDCl$_3$: δ=7.26, 77.02; DMSO-d$_6$: δ=2.50, 39.99). Splitting patterns describe apparent multiplicities and are designated as s (singlet), br s (broad singlet), d (doublet), dd (doublet of doublet), t (triplet), q (quartet), m (multiplet). Coupling constants (J) are given in Hertz (Hz). Purity of all compounds used in biological assays was ≥95% as measured by LC/MS Finnigan Surveyor MSQ Plus (Thermo Fisher Scientific, Dreieich, Germany).

The system consists of LC pump, autosampler, PDA detector, and single-quadrupole MS detector, as well as the standard software Xcalibur for operation. RP C18 Nucleodur 100-5 (125×3 mm) column (Macherey-Nagel GmbH, Dühren, Germany) was used as stationary phase, and a binary solvent system A and B (A=water with 0.1% TFA; B=MeCN with 0.1% TFA) was used as mobile phase. In a gradient run the percentage of B was increased from an initial concentration of 0% at 0 min to 100% at 15 min and kept at 100% for 5 min. The injection volume was 10 μL and flow rate was set to 800 μL/min. MS (ESI) analysis was carried out at a spray voltage of 3800 V, a capillary temperature of 350° C. and a source CID of 10 V. Spectra were acquired in positive mode from 100 to 1000 m/z and at 254 nm for UV tracing.

3.5.2. General Synthetic Procedures a) A mixture of the acid (25 mmol), isopropyl bromide (52 mmol) and potassium carbonate (52 mmol) in 100 ml DMF were heated overnight at 90° C. Excess DMF was then removed under reduced pressure and the remaining residue was partitioned between water and ethyl acetate. The organic layer was dried over sodium sulphate and the excess solvent was then removed under reduced pressure to give the pure product.

b) To a stirred solution of the nitro derivative (10 mmol) in EtOH (60 mL), iron powder (2.80 g, 50 mmol) was added at 55° C. followed by NH$_4$Cl (266 mg, 5 mmol) solution in water (30 mL). The reaction was refluxed for 1-2 h, then iron was filtered while hot and the filtrate was concentrated under vacuum till dryness. The residue was diluted with water (30 mL) and basified by NaHCO$_3$ (saturated aqueous solution) to pH 7-8. The mixture was extracted with EtOAc. The combined organic extract was washed with brine, dried (MgSO$_4$), and the solvent was removed by vacuum distillation. The obtained crude material was triturated with n-hexane, and collected by filtration.

f) To a stirred solution of the aldehyde (4 mmol), and NaOH (0.8 g, 20 mmol) in water (50 mL), AgNO$_3$ (3.4 g, 20 mmol) was added portion wise. The reaction was refluxed overnight, then allowed to cool and filtered through celite. Filtrate was cooled in an ice bath and acidified with HCl 37% to pH 3-4. The precipitated solid was collected by filtration, washed with cold water then n-hexane.

h) To a stirred solution of the acid (2 mmol), amine (2.4 mmol) in anhydrous CHCl$_3$ (50 mL) under a nitrogen atmosphere, dichlorotriphenylphosphorane (3.0 g, 9 mmol) was added. The reaction was heated at 80° C. for 5 h. Solvent was removed by vacuum distillation. The residue was then purified using flash chromatography.

i) Amide formation was done according to the following reported procedure.[1] A boiling solution of the acid (1 mmol) and the amine (1 mmol) in xylenes 2.5 ml was treated with a 2M solution of PCl$_3$ in CH$_2$Cl$_2$ (0.4 mmol). After 2 hours the excess solvent was evaporated and the residue was purified using column chromatography.

j) Ester hydrolysis was done according to the following reported procedure.[2] The ester (0.1 mmol), sodium hydroxide 1M (3 mL) and anhydrous methanol were heated overnight at 45° C. On cooling, the reaction mixture was acidified to pH 1 (3 mL, hydrochloric acid 1 M) and extracted with dichloromethane (3×150 mL). The organic was dried over sodium sulphate and the solvent removed under reduced pressure to give the pure product.

3.5.3. Specific Synthetic Procedures:

2-formyl-6-methoxyphenyl acetate

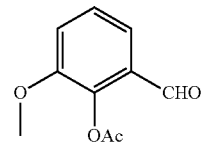

To a stirred solution of 3-methoxysalicylaldehyde (4.56 g, 30 mmol), and pyridine (2.43 mL, 30 mmol) in DCM (40 mL), acetyl chloride (2.36 g, 30 mmol) was added drop wise. The reaction was stirred at room temperature overnight then the solvent was removed by vacuum distillation. The residue was triturated in cold dil. HCl and filtered, washed with cold water then n-hexane.

Yield 94% (off-white solid), m/z (ESI+) 195 [M+H]$^+$.

6-formyl-2-methoxy-3-nitrophenyl acetate

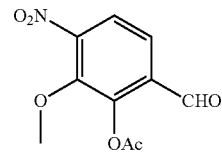 [SMILES: COc1c([N+](=O)[O-])ccc(C=O)c1OC(C)=O]

To a stirred ice-cooled suspension of 2-formyl-6-methoxyphenyl acetate (1.94 g, 10 mmol), and KNO$_3$ (1.01 g, 10 mmol) in CHCl$_3$ (15 mL), trifluoroacetic anhydride (12 mL) was added. The reaction was stirred in an ice bath for 2 h. then at room temperature overnight. The reaction was diluted very carefully with water (50 mL) and extracted with CHCl$_3$. The combined organic extract was dried (MgSO$_4$), and the solvent was removed by vacuum distillation. The residue was dissolved in toluene and purified using flash chromatography (SiO$_2$, n-hexane-EtOAc=3:1). Yield 45% (yellow semisolid), m/z (ESI+) 239 [M]+.

2-hydroxy-3-methoxy-4-nitrobenzaldehyde

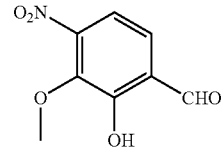

To a stirred suspension of 6-formyl-2-methoxy-3-nitrophenyl acetate (957 mg, 4 mmol) in water (30 mL), NaOH (0.8 g, 20 mmol) was added. The reaction was refluxed for 2 h then allowed to stir at room temperature overnight. The solution was cooled in an ice bath and acidified by HCl 2 M to pH 3-4. The precipitated solid was collected by filtration, washed with cold water then n-hexane. Yield 90% (yellowish brown solid), m/z (ESI+) 197 [M]$^+$.

2,3-Dihydroxy-4-nitrobenzaldehyde

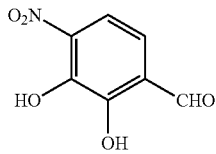 [SMILES: O=Cc1ccc([N+](=O)[O-])c(O)c1O]

To a stirred solution of 18 (1.2 g, 5 mmol) in DCM (10 mL) cooled at 0° C. in an ice bath, BBr₃ (1 M solution in DCM, 20 mL) was added carefully under a nitrogen atmosphere. The reaction mixture was allowed to warm to room temperature and was further stirred overnight. Solvent was removed in vacuo. The residue was cautiously diluted with water (50 mL) and medium was acidified by 2 N HCl to pH 4-5, if needed. The mixture was extracted with EtOAc (3×30 mL). The combined organic extract was washed with brine, dried over anhydrous MgSO₄, and the solvent was removed by vacuum distillation. The residue was dissolved in CHCl₃ and purified using flash chromatography (SiO₂, DCM-MeOH=98:2).

3.5.4. Experimental Data for Derivatives (1s-4s)

4-(4-(4-Aminobenzamido)-2-hydroxy-3-methoxy-benzamido)-3-isopropoxybenzoic acid (1s)

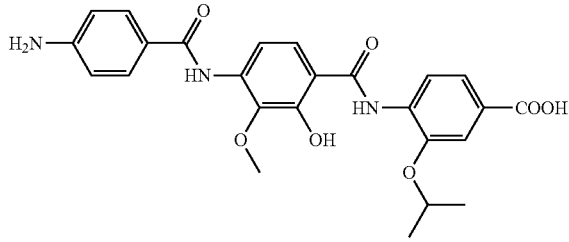 [SMILES: COc1c(NC(=O)c2ccc(N)cc2)ccc(C(=O)Nc2ccc(C(=O)O)cc2OC(C)C)c1O]

Yield 85%; pale yellow crystals; $^1$H NMR (500 MHz, DMSO-$d_6$) δ 12.79 (br s, 1H), 11.38 (br s, 1H), 10.98 (br s, 1H), 9.22 (br s, 1H), 8.56 (d, J=8.5 Hz, 1H), 7.80 (d, J=8.8 Hz, 1H), 7.73 (d, J=8.5 Hz, 2H), 7.65 (d, J=8.8 Hz, 1H), 7.59 (dd, J=8.5, 1.6 Hz, 1H), 7.57 (d, J=1.6 Hz, 1H), 6.69 (d, J=8.5 Hz, 2H), 5.39 (br s, 2H), 4.76 (septet, J=6.0 Hz, 1H), 3.78 (s, 3H), 1.39 (d, J=6.0 Hz, 6H); $^{13}$C NMR (126 MHz, DMSO-$d_6$) δ 166.99, 165.03, 163.28, 151.46, 149.53, 146.13, 139.38, 136.34, 133.45, 129.43, 125.62, 125.55, 122.65, 121.21, 119.28, 115.71, 113.89, 113.75, 113.43, 71.72, 60.40, 21.73; m/z (ESI+) 479.99 [M+H]$^+$; $t_R$=14.53 min.

4-(4-(4-Aminobenzamido)-2,3-diisopropoxybenzamido)-3-isopropoxybenzoic acid (2s)

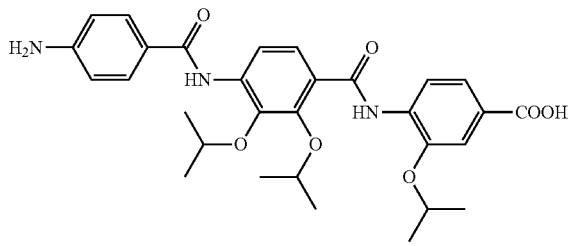 [SMILES: CC(C)Oc1cc(C(=O)O)ccc1NC(=O)c1ccc(NC(=O)c2ccc(N)cc2)c(OC(C)C)c1OC(C)C]

Yield 81%; beige solid; $^1$H NMR (500 MHz, DMSO-$d_6$) δ 12.82 (br s, 1H), 10.36 (br s, 1H), 9.06 (br s, 1H), 8.60 (d, J=8.5 Hz, 1H), 8.01 (d, J=8.8 Hz, 1H), 7.75 (d, J=8.8 Hz, 1H), 7.70 (d, J=8.8 Hz, 2H), 7.61 (dd, J=8.5, 1.9 Hz, 1H), 7.58 (d, J=1.9 Hz, 1H), 6.63 (d, J=8.8 Hz, 2H), 5.90 (br s, 2H), 4.75 (septet, J=6.0 Hz, 1H), 4.63 (septet, J=6.3 Hz, 1H), 4.52 (septet, J=6.0 Hz, 1H), 1.35 (d, J=6.0 Hz, 6H), 1.31 (d, J=6.0 Hz, 6H), 1.27 (d, J=6.3 Hz, 6H); $^{13}$C NMR (126 MHz, DMSO-$d_6$) δ 166.88, 164.45, 162.79, 152.66, 148.60, 145.71, 141.15, 137.69, 132.89, 129.08, 125.58, 125.44, 123.52, 122.83, 119.87, 118.64, 117.50, 113.94, 112.87, 77.12, 75.70, 72.02, 22.25, 21.90, 21.79; m/z (ESI+) 549.86 [M+H]$^+$; $t_R$=13.10 min.

4-(4-(4-aminobenzamido)-3-hydroxy-2-methoxybenzamido)-3-isopropoxybenzoic acid (3s)

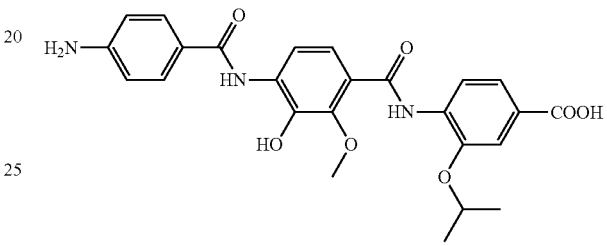

Yield 79%; beige solid; $^1$H NMR (500 MHz, DMSO-$d_6$) δ 12.67 (br s, 1H), 10.90 (s, 1H), 10.12 (s, 1H), 9.73 (s, 1H), 8.65 (d, J=8.4 Hz, 1H), 7.80-7.71 (m, 2H), 7.64-7.54 (m, 4H), 6.67-6.59 (m, 2H), 5.95 (br s, 2H), 4.86 (septet, J=6.2 Hz, 1H), 3.99 (s, 3H), 1.41 (d, J=6.0 Hz, 6H); 13C NMR (126 MHz, DMSO-$d_6$) δ 166.97, 166.24, 162.25, 152.99, 147.98, 145.57, 141.60, 133.01, 132.60, 129.79, 125.45, 122.58, 121.24, 119.02, 118.71, 118.20, 112.99, 112.96, 112.69, 71.00, 61.60, 21.71. m/z (ESI+) 480.08 [M+H]+; tR=10.70 min.

4-(4-(4-Aminobenzamido)-3-isopropoxy-2-methoxybenzamido)-3-isopropoxybenzoic acid (4s)

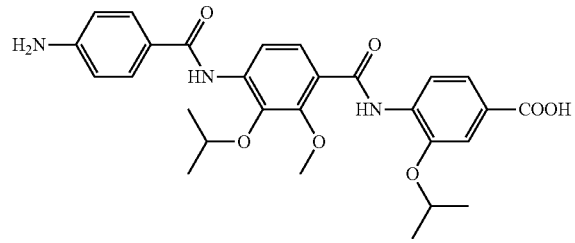 [SMILES: COc1c(C(=O)Nc2ccc(C(=O)O)cc2OC(C)C)ccc(NC(=O)c2ccc(N)cc2)c1OC(C)C]

Yield 43%; beige solid; $^1$H NMR (500 MHz, DMSO-$d_6$) δ 12.82 (br s, 1H), 10.90 (br s, 1H), 9.09 (br s, 1H), 8.62 (d, J=8.2 Hz, 1H), 8.06 (d, J=8.8 Hz, 1H), 7.84 (d, J=8.8 Hz, 1H), 7.70 (d, J=8.5 Hz, 2H), 7.60 (dd, J=8.2, 1.6 Hz, 1H), 7.58 (d, J=1.6 Hz, 1H), 6.63 (d, J=8.5 Hz, 2H), 5.92 (br s, 2H), 4.85 (septet, J=6.0 Hz, 1H), 4.47 (septet, J=6.0 Hz, 1H), 4.04 (s, 3H), 1.40 (d, J=6.0 Hz, 6H), 1.32 (d, J=6.0 Hz, 6H); $^{13}$C NMR (126 MHz, DMSO-$d_6$) δ 166.96, 164.45, 161.87, 152.74, 151.59, 145.55, 140.72, 138.04, 133.03, 129.11, 125.79, 125.47, 122.67, 120.61, 119.78, 118.58, 117.31, 113.14, 112.87, 76.50, 71.14, 61.78, 22.36, 21.66; m/z (ESI+) 522.04 [M+H]$^+$; $t_R$=15.58 min.

REFERENCES

1) Alina Fomovska, Richard D. Wood, Ernest Mui, Jitenter P. Dubey, Leandra R. Ferreira, Mark R. Hickman, Patricia J. Lee, Susan E. Leed, Jennifer M. Auschwitz, William J. Welsh, Caroline Sommerville, Stuart Woods, Craig Roberts, and Rima McLeod. *Salicylanilide Inhibitors of Toxoplasma gondii*. J. Med. Chem., 2012, 55 (19), pp 8375-8391.
2) Valeria Azzarito, Panchami Prabhakaran, Alice I. Bartlett, Natasha Murphy, Michaele J. Hardie, Colin A. Kilner, Thomas A. Edwards, Stuart L. Warriner, Andrew J. Wilson. *2-O-Alkylated Para-Benzamide α-Helix Mimetics: The Role of Scaffold Curvature*. Org. Biomol. Chem., 2012, 10, 6469.

The invention claimed is:

1. A method for treating a subject suffering from or susceptible to a bacterial infection, the method comprising:
administering an effective amount of a compound to the subject,
wherein the compound has the formula (I):

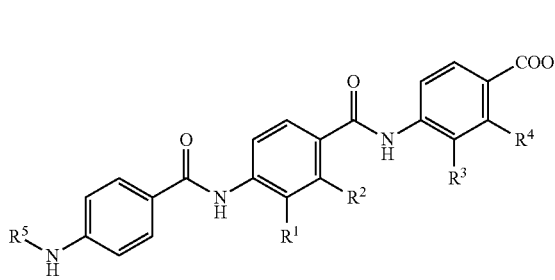

(I)

wherein
$R^1$ is hydrogen, OH or a group of formula —O—$C_{1-6}$ alkyl;
$R^2$ is hydrogen, OH or a group of formula —O—$C_{1-6}$ alkyl;
$R^3$ is hydrogen, OH or a group of formula —O—$C_{1-6}$ alkyl;
$R^4$ is hydrogen, OH or a group of formula —O—$C_{1-6}$ alkyl; and
$R^5$ is a group of the following formula:

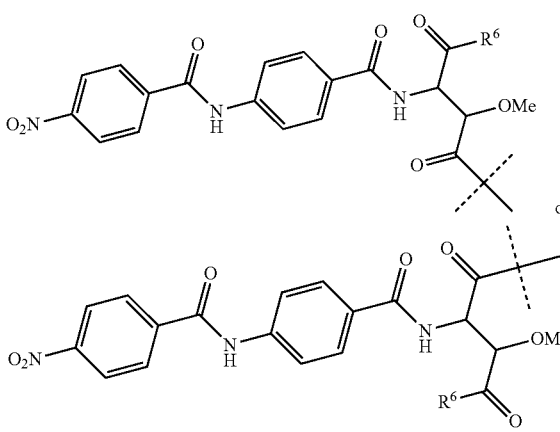

wherein $R^6$ is OH or $NH_2$;
or a pharmaceutically acceptable salt, or a pharmaceutically acceptable formulation thereof.

2. The method of claim 1, wherein
$R^1$ is hydrogen, OH or a group of formula —O—$C_{1-4}$ alkyl;
$R^2$ is hydrogen, OH or a group of formula —O—$C_{1-4}$ alkyl;
$R^3$ is hydrogen, OH or a group of formula —O—$C_{1-4}$ alkyl;
$R^4$ is hydrogen, OH or a group of formula —O—$C_{1-4}$ alkyl; and
$R^5$ is a group of the following formula:

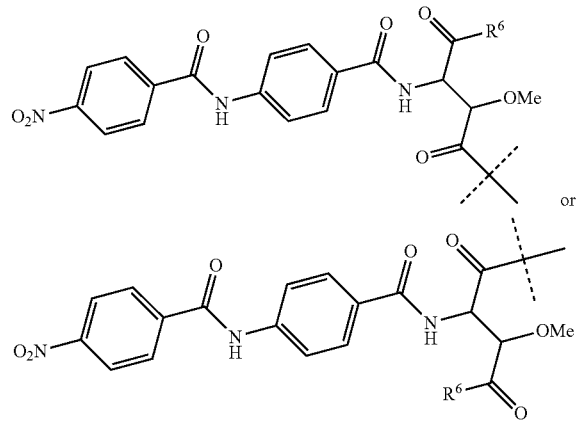

wherein $R^6$ is OH or $NH_2$;
or a pharmaceutically acceptable salt, or a pharmaceutically acceptable formulation thereof.

3. The method of claim 1, wherein $R^1$ is OH.
4. The method of claim 1, wherein $R^1$ is a group of formula —O—$C_{1-4}$ alkyl; especially wherein $R^1$ is a group of formula —O—$CH(CH_3)_2$.
5. The method of claim 1, $R^2$ is hydrogen.
6. The method of claim 1, wherein $R^2$ is OH.
7. The method of claim 1, wherein $R^3$ is hydrogen.
8. The method of claim 1, wherein $R^3$ is OH.
9. The method of claim 1, wherein $R^3$ is a group of formula —O—$C_{1-4}$ alkyl.
10. The method of claim 1, wherein $R^4$ is hydrogen.
11. The method of claim 1, wherein $R^4$ is OH.
12. The method of claim 1, wherein $R^5$ is a group of the following formula:

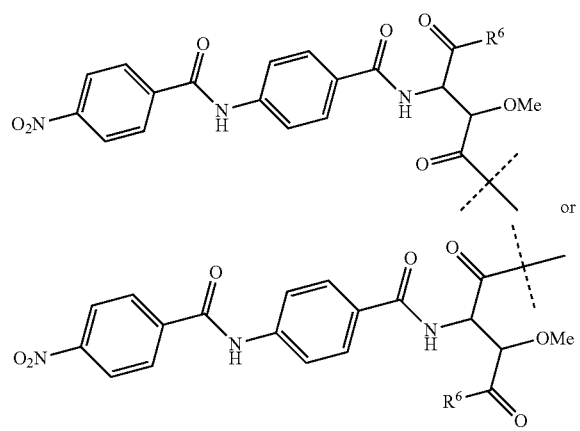

wherein $R^6$ is OH or $NH_2$.

13. The method of claim 1, wherein the compound is selected from the group consisting of following compounds:
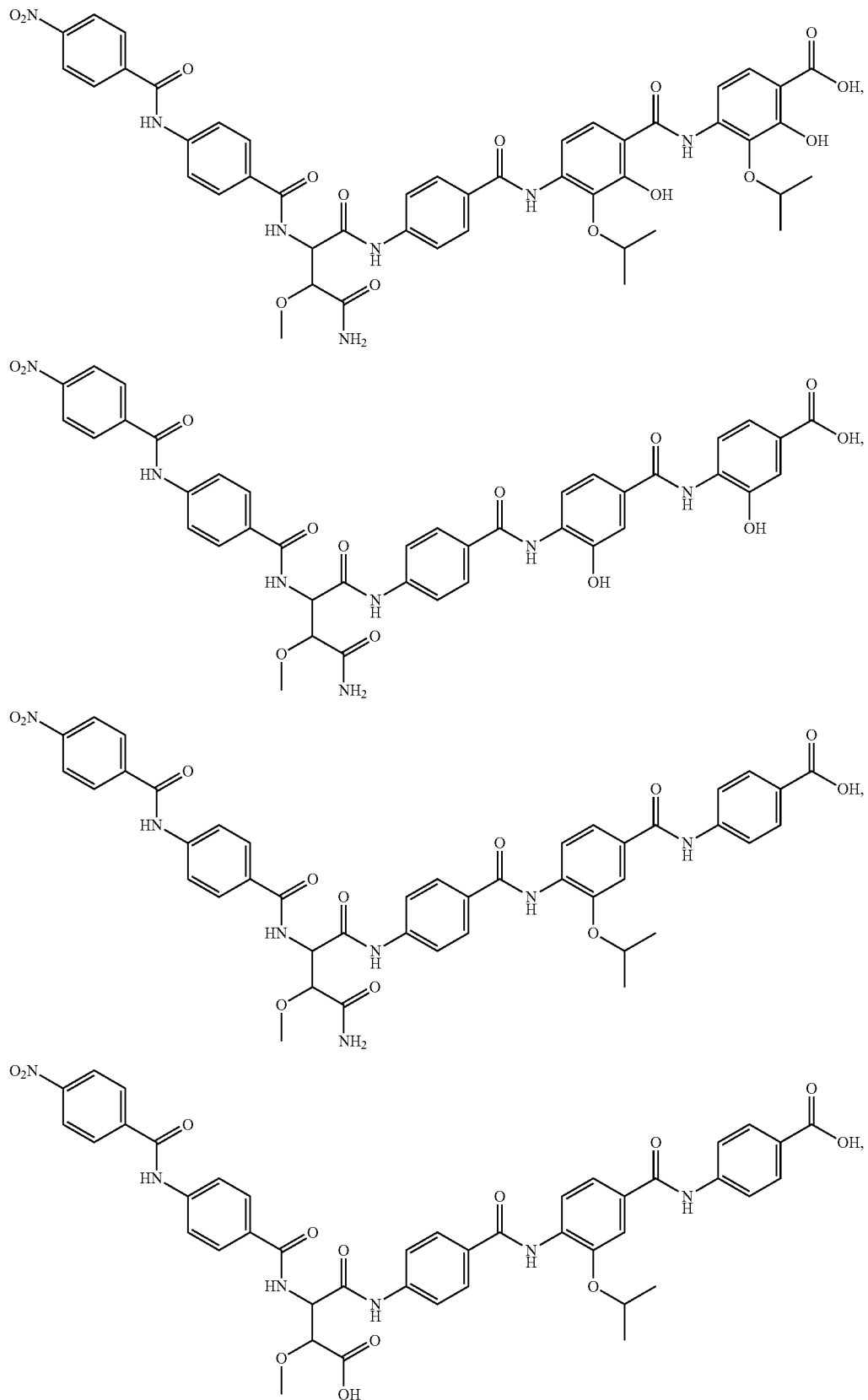

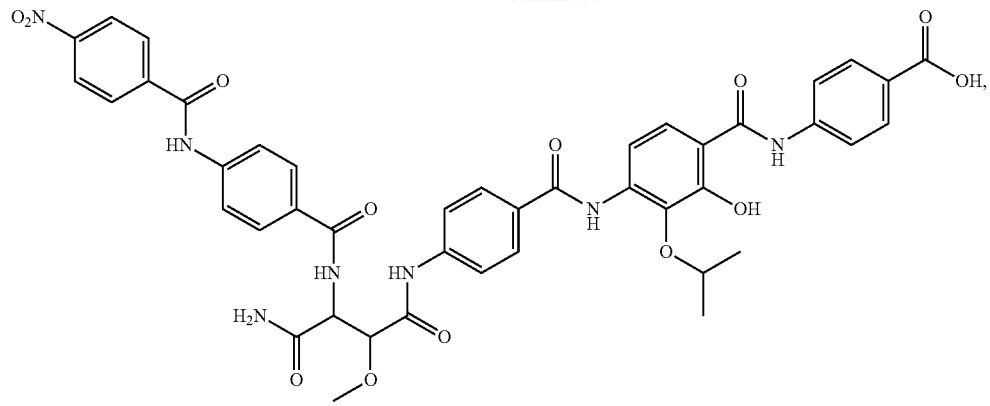
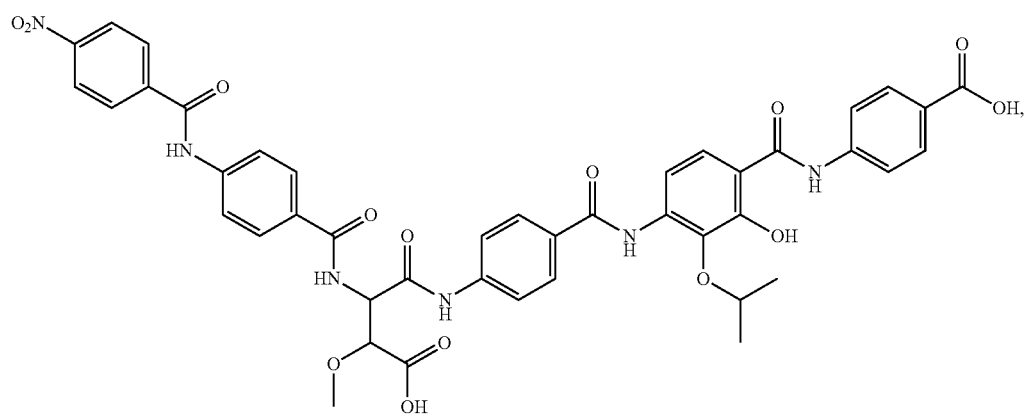
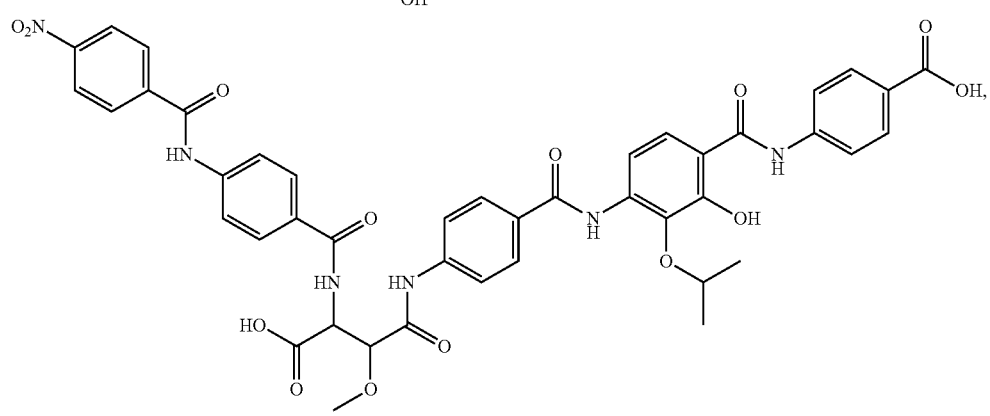
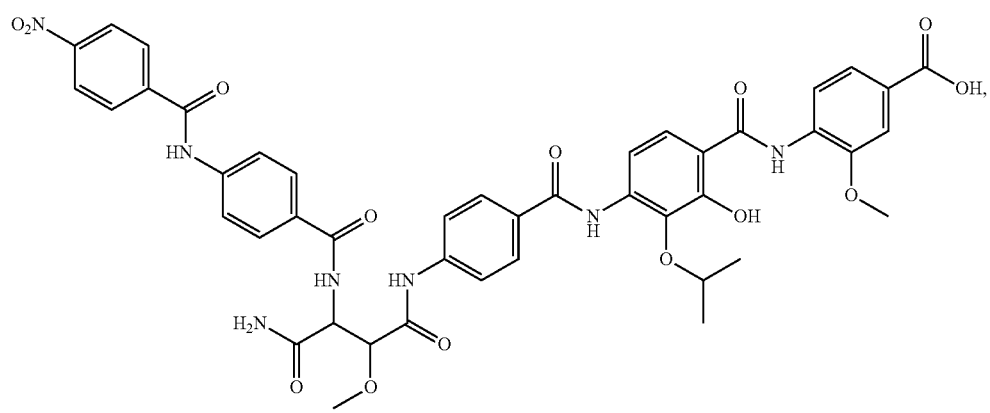

-continued
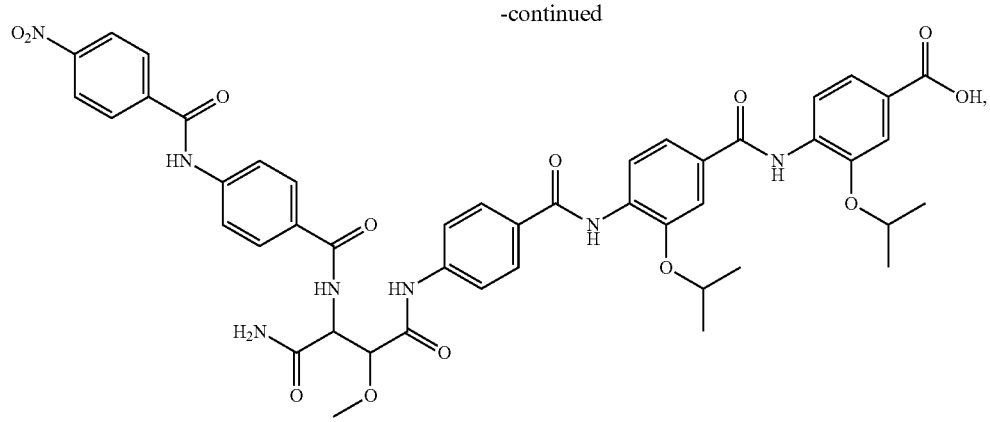
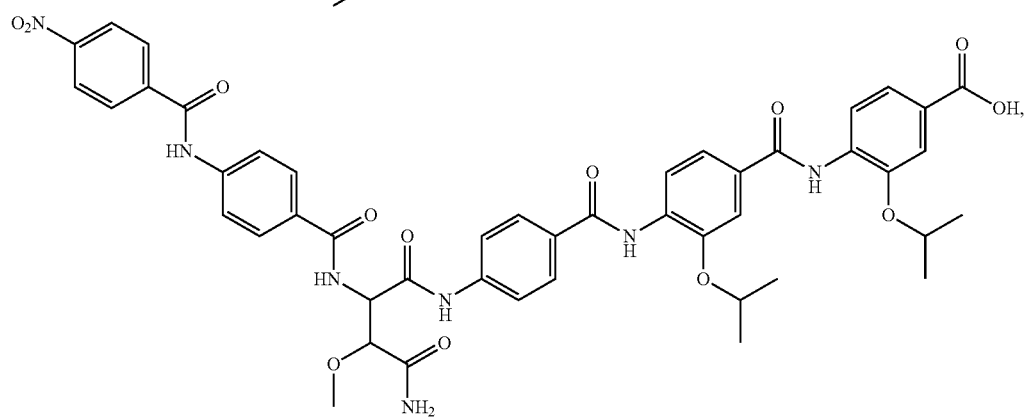
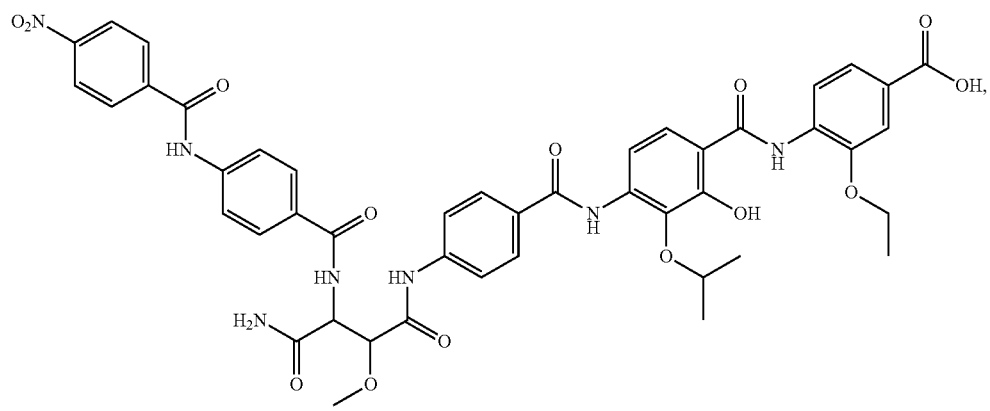
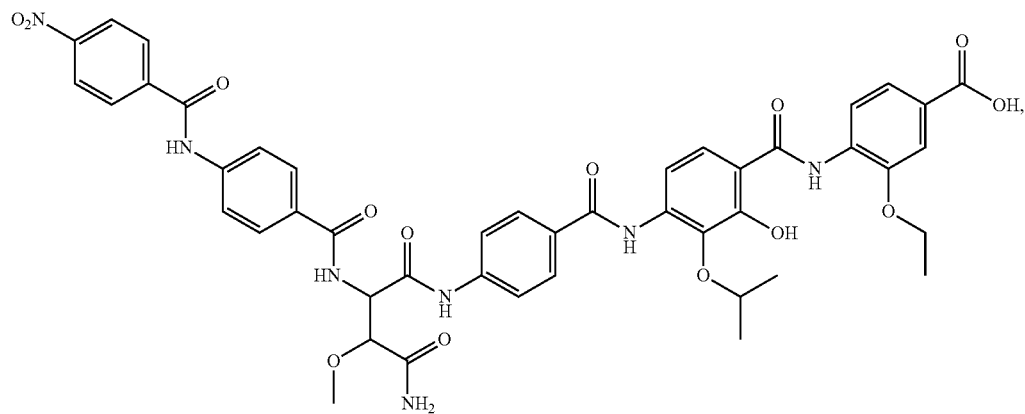 [SMILES: COC(C(N)=O)C(NC(=O)c1ccc(NC(=O)c2ccc([N+](=O)[O-])cc2)cc1)C(=O)Nc1ccc(C(=O)Nc2ccc(C(=O)Nc3ccc(C(=O)O)cc3)c(O)c2)cc1]

-continued
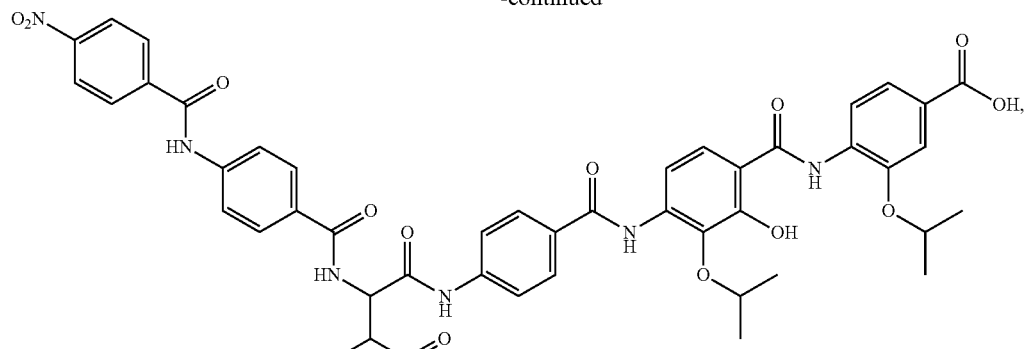
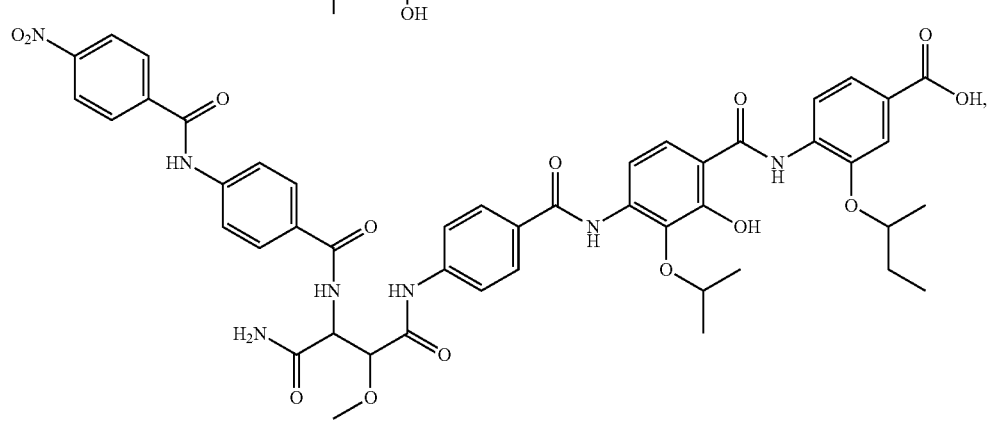
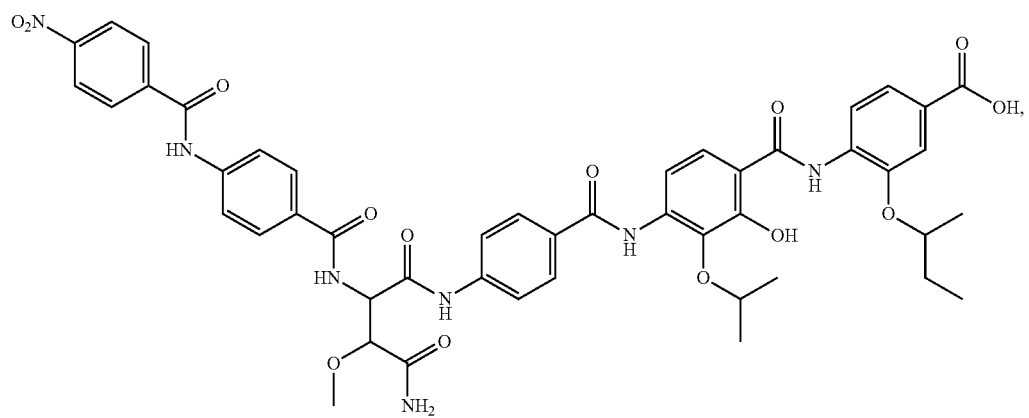
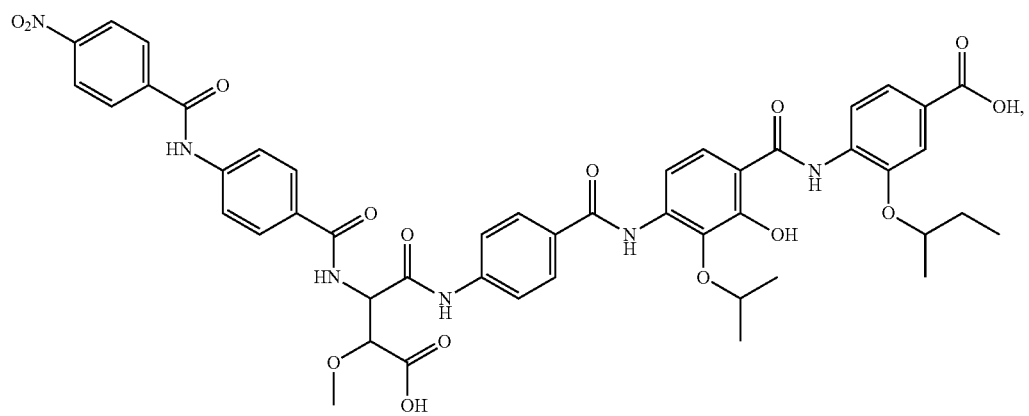

-continued

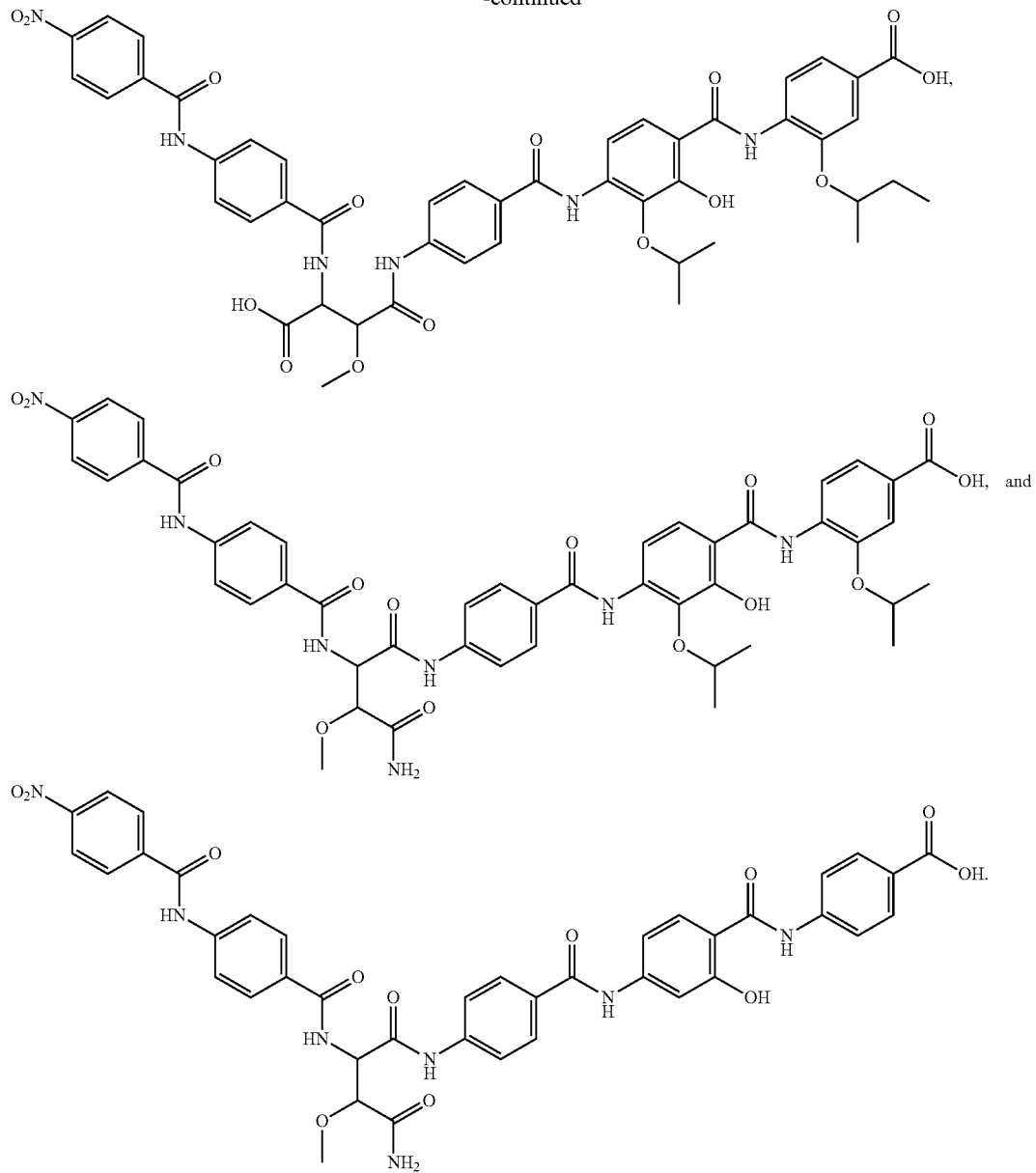

14. The method of claim 1 wherein the subject is suffering from a Gram-positive bacterial infection.

15. The method of claim 1 wherein the subject is suffering from a Gram-negative bacterial infection.

16. The method of claim 1 wherein the subject is suffering from an infection caused by *Pseudomonas aeruginosa* bacterial infection.

17. The method of claim 1 wherein the subject is suffering from an infection caused by *E. coli, Pseudomonas aeruginosa* or *A baumannii*.

* * * * *